United States Patent [19]
Kitto et al.

[11] Patent Number: 5,118,610
[45] Date of Patent: Jun. 2, 1992

[54] TECHNIQUES FOR DETECTING INSECT CONTAMINATION OF FOODSTUFFS

[75] Inventors: G. Barrie Kitto; Frank A. Quinn, both of Austin, Tex.; Wendell Burkholder, Madison, Wis.

[73] Assignees: Board of Regents, The University of Texas System, Austin, Tex.; The United States of America as represented by the Secretary of Agriculture, Washington, D.C.

[21] Appl. No.: 443,945

[22] Filed: Nov. 30, 1989

[51] Int. Cl.⁵ .......................... G01N 33/543
[52] U.S. Cl. .................... 435/7.21; 435/7.5; 435/7.92; 435/7.94; 435/962; 435/975; 436/518; 436/536; 436/548
[58] Field of Search ............. 435/7.21, 7.22, 7.31, 435/7.5, 7.92, 962, 975, 810, 7.94; 436/518, 536, 548

[56] References Cited

PUBLICATIONS

Schoeckenstein et al. *J. Allergy Clin. Immunol.* 82(6): 1081, 1988.
Mitsuhashi et al. *Int. Arch. Allergy Appl. Immunol.* 72(4):310, 1983.
Nakamori et al. *Jpn J. Thorac Dis.* 20(11):1163, 1982.
Bullard et al. *J. Mol. Biol.* 115(3):417, 1977.
Levine et al. *Meth. Enzymol.* 85:149, 1982.
Yolken et al. *Rev. Inf. Diseases* 4(1):35, 1982.

Primary Examiner—David Saunders
Attorney, Agent, or Firm—Arnold, White & Durkee

[57] ABSTRACT

The present invention involves approaches to the detection of insect contamination of foodstuffs such as grain, for example. These approaches involve the detection of biological substances characteristic of insects. One such approach is an assay for the insect exoskeleton material, chitin. This test is particularly suited to the detection of live or dead specimens of the adult or egg stages of insects and for insect parts. Another type of assay uses an immunological approach to the detection and quantitation of an insect-specific protein such as the insect muscle protein, myosin or components thereof, for example. This type of test is well suited for detecting all stages of insect development from egg to adult, whether live or dead. It should also provide an assay system that correlates well to the current insect fragment assay.

32 Claims, 16 Drawing Sheets

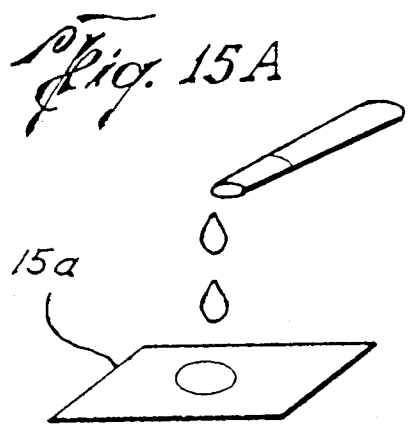
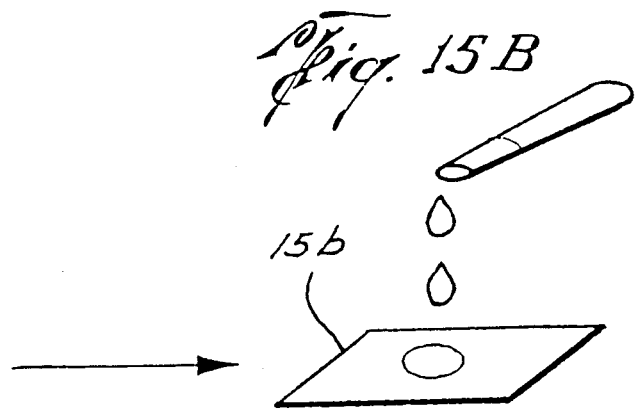
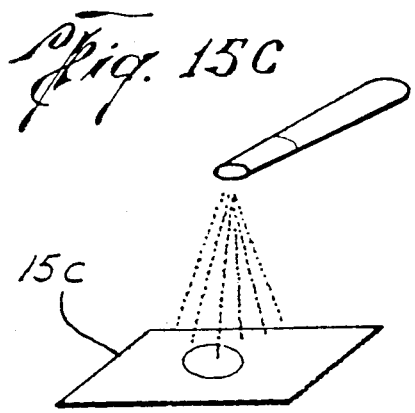
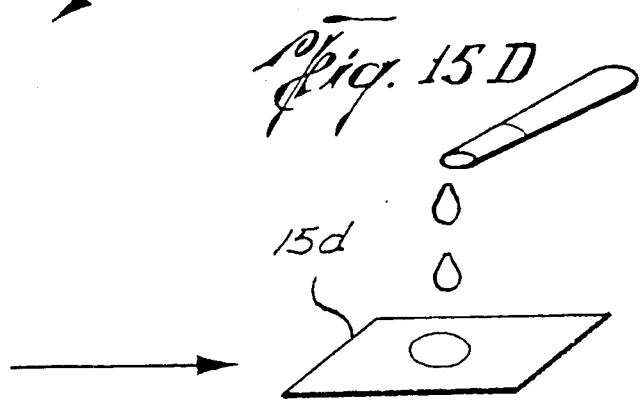
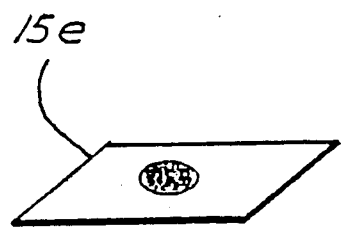

⊥ = ANTI-GRANARY WEEVIL MYOSIN ANTIBODY

⊥ᴱ = ENZYME LABELLED ANTI-GRANARY WEEVIL MYOSIN ANTIBODY

● = COLORED PRODUCT

M = MYOSIN

S = SUBSTRATE

• 15 MINUTES    ○ 20 MINUTES

• Ab-HRP 1:1000   ○ Ab-HRP 1:500   △ Ab-HRP 1:250

• 75 ng     ○ 50 ng
△ 25 ng

TECHNIQUES FOR DETECTING INSECT CONTAMINATION OF FOODSTUFFS

Research relating to the present application supported by Contract No. 58-114-1003 from the United States Department of Agriculture.

BACKGROUND OF THE INVENTION

The present invention relates to techniques for detection and identification of biological contaminants in vegetable foodstuffs. More particularly, the present invention involves the detection of insects or insect parts in whole or milled grain.

The detection of insects in stored grain and the quantitation of insect parts present in milled grain products represents a serious and continuing problem for the cereal industry. Present methods of detection primarily involve visual inspection [usually microscopic] (1, 2) and x-ray analysis (3) which require trained personnel and are time-consuming, difficult to standardize and expensive.

A variety of approaches have been used in the past to attempt development of efficient assay procedures, but none of these has proven particularly satisfactory for routine testing. These methods have included the use of nuclear magnetic resonance (4, 5, 6), sound amplification (7), infrared spectrometry (8), and chemical techniques (9). These techniques have tended to be too expensive, technically difficult and also difficult to quantify and identify the specific infestation detected. For example, sound amplification techniques (10-12) show promise for the detection of live insects in grain but provide little quantitative analysis, and are unable to detect eggs, dead insects or insect part contamination. The preferred characteristics of assays for insect contamination are as follows: it should be highly specific, be very sensitive, rapid, and inexpensive. Moreover, it ideally should be employable by persons having minimal training, particularly in non-laboratory settings, e.g., at grain elevator and mill sites.

The present invention involves approaches to the detection of insect contamination of foodstuffs such as grain, beans (e.g., coffee), spices or even viable crops (e.g., corn, etc.). These approaches involve the detection or discrimination of biological substances specific to insects and usually absent in pure foodstuffs. One such approach is an assay for the insect exoskeleton material, chitin. This test is particularly suited to the detection of live or dead specimens of the adult stages of insects and for insect parts. Another type of assay uses an immunological approach for the detection and quantitation of an insect-specific protein such as the insect muscle protein, myosin or components thereof, for example. This type of test is well suited for detecting all stages of insect development from egg to adult, whether live or dead. It should also provide an assay system that correlates well to the current insect fragment assay and whole insect analysis (eggs to adults).

Chitin is the major structural material of insect exoskeletons. This material is a beta-[1–4]-homopolymer of N-acetylglucosamine, as shown in FIG. 1. Chitin is not found in higher plants. Because of the relatively large amounts of chitin associated with the pupal and adult stages of insects, sensitive biochemical tests for chitin should provide a good means of assaying for the presence of both live and dead insect remains in plant material. Chitin may also be found in certain molds and fungi which could be an important consideration in some circumstances.

Very sensitive and rapid procedures are available for assaying for chitin. Such tests can be modified for successful determination of grain or grain product insect infestation. The most sensitive test procedures for chitin involve hydrolysis of the chitin to N-acetylglucosamine and subsequent assay for the latter compound. Several chemical degradation procedures for chitin hydrolysis have been tested and several N-acetylglucosamine tests evaluated for their suitability for grain assays. One sensitive and reliable assay technique described herein uses an alkaline hydrolysis procedure and has a current detection limit of approximately $1 \times 10^{-9}$ moles of N-acetylglucosamine (NAG). The average grain weevil contains approximately $1.12 \times 10^{-6}$ moles of NAG, which is 1000 times more NAG than is needed for a positive test. The major potential disadvantage of this assay is that it is rather lengthy and requires the use of harsh chemicals. It is clear that the procedures described herein offer a very sensitive means for grain analysis. The further adaptation of chitin assays for low cost and rapid analysis is an object of the present invention.

Immunological assays have found widespread use in clinical diagnostic settings (13), and are also becoming available for in home use, particularly for the early detection of pregnancy (14). The vast potential of these procedures for non-medical purposes has been the subject of increasing study over the last few years. Nowhere is this more evident than in the explosion of commercial uses being developed for the enzyme linked immunosorbent assays (ELISA), which are rapidly becoming standard procedure in a variety of settings (15).

In order to develop an optimal immunological assay for an insect contamination of foodstuffs, antibodies are required which are directed against an insect-specific antigen, preferably protein, likely to be present in any life stage of the contaminating insect or in insect remains. Necessarily, the antisera should not cross-react with any plant material present. For an immunoassay with broad insect-specificity, it would also be preferable to use as an antigen, a protein that is very slowly evolving. Antibodies directed against such an insect-specific protein of one species would cross-react with the same protein in a wide variety of insect species. One such protein is the insect muscle protein myosin. Myosin and components thereof are ubiquitous in insects. Myosin is present in large quantities in adult insect tissue, and is also present in appreciable quantities in other life stages. Finally, myosin is a very slowly evolving protein (16). To develop an immunoassay specific for a particular species of insect contamination, antibodies having a unique species-specificity could be prepared and used. For example, polyclonal or monoclonal antibody could be developed which is directed toward an antigen specifically characterizing a single insect species. Alternatively, polyclonal antibodies, monoclonal antibodies or mixtures thereof could be developed which recognize an epitope of an insect antigen which is common to several or all insect species of interest. Such a broadly specific monoclonal antibody could also serve in reproducible insect assays. Monoclonal antibodies provide a dependable source of identical antibodies.

SUMMARY OF THE INVENTION

The present invention involves methods for determining the estimated degree of insect contamination in a foodstuff such as whole or milled grain, for example. One of these methods involves a sensitive assay for insect-specific biological molecules. For example, assaying chitin content in a sample of said foodstuff may be utilized as a measure of insect presence. Chitin may be assayed directly or indirectly. After an assay of chitin content, the estimated degree of insect contamination in said foodstuff may be calculated from said chitin content.

The insects at all life stages or parts thereof contaminating a foodstuff include, for example: *Sitophilus zeamais; Sitophilus granarius; Sitophilus oryzae; Trogoderma variabile; Trogoderma glabrum; Tribolium castaneum; Tribolium confusem; Oryzaephilus mercator; Oryzaephilus surinamensis; Rhyzopertha dominica; Prostephanus truncatus; Lasioderma serricorne; Stegobium paniceum; Callosobruchus maculatus; Attagenus mecatoma; Alphitobius diaperinus;* and *Plodia interpunctella.*

A preferred method of chitin analysis according to the present invention involves the hydrolysis of chitin in foodstuffs such as grain, for example, to N-acetylglucosamine. The N-acetylglucosamine may then be analyzed in a manner both accurate and convenient. The N-acetylglucosamine assay is preferably colorimetric but might be enzymatic. A sample of said foodstuff is initially subjected to conditions sufficient to hydrolyze chitin contained therein to N-acetylglucosamine. The sample of said foodstuff may be subjected to conditions sufficient to chemically or enzymatically hydrolyze any chitin contained therein to N-acetylglucosamine. Chemical chitin hydrolysis may be by acid or alkali, for example. Enzymatic hydrolysis of chitin by a mixture comprising chitinase and chitobiase is a preferred method of obtaining N-acetylglucosamine. A mixture containing these enzymes is obtainable from almonds. After an assay for N-acetylglucosamine content in such a sample hydrolysate, the N-acetylglucosamine content, being a chitin product, may be correlated with the estimated degree of insect contamination in said foodstuff.

In another aspect, the present invention may involve a kit useful for the detection of insect contamination in a foodstuff. Such a kit would comprise: 1) a carrier being compartmentalized to receive one or more container means in close confinement therein; 2) a first container means comprising at least one enzyme capable of hydrolyzing chitin to N-acetylglucosamine; and 3) a second container means comprising reagents for colorimetric analysis of N-acetylglucosamine. The first container preferably comprises chitobiase and chitinase.

The present invention, in one preferred embodiment, involves an immunochemical method for determining the estimated degree of insect contamination in a foodstuff. This method, in this preferred embodiment, comprises the following steps: 1) assaying the content of insect myosin or components thereof in a sample of said foodstuff; and 2) calculating from said insect myosin or component content the estimated degree of insect contamination in said foodstuff.

A second and more general embodiment of an immunochemical method for determining the estimated degree of insect contamination in a foodstuff comprises the following steps: 1) obtaining an antibody specifically binding an insect antigen, preferably a protein antigen; 2) incubating a sample of said foodstuff with the antibody; 3) assaying antibody-sample interaction and correlating said interaction with the estimated degree of insect contamination in said foodstuff. While the insect antigen is preferably protein, it is most preferably the protein myosin, or components thereof.

In another view, the methods of the present invention for determining the estimated degree of insect contamination in a foodstuff may involve any method for assaying the amount of insect myosin or its components thereof in the foodstuff. Such a method would comprise: 1) subjecting a sample of said foodstuff to conditions sufficient to at least partially solubilize any insect myosin or components thereof contained therein; 2) assaying insect myosin or content of said sample; and 3) correlating the myosin components content with the estimated degree of insect contamination in said foodstuff.

The foodstuff of the above methods may be a whole or milled grain or any other material for which the degree of insect contamination is desired. The antibodies usable in the present methods of determining insect contamination are preferably one or more monoclonal types but may be polyclonal, as well as a mixture of one or both.

A kit useful for the immunochemical detection of insect contamination in a foodstuff may comprise: 1) a carrier compartmentalized to receive one or more container means in close confinement therein; 2) a first container means comprising an antibody specifically binding an insect antigen, said antibody being specifically or non specifically attached to a solid matrix; and 3) a second container means comprising detectably labeled antibody specific for said insect antigen.

An immunochemical kit useful for the detection of insect contamination in a foodstuff may also be described as one which comprises: 1) a carrier compartmentalized to receive one or more container means in close confinement therein; 2) a first container means comprising an antibody from a first antibody-producing species, said antibody specifically binding insect antigen and being specifically or non specifically attached to a solid matrix; and 3) a second container means comprising a detectably labeled antibody from a second antibody-producing species, said detectably labeled antibody specifically binding antibody from the first antibody-producing species. In these immunochemical kits the preferred insect antigen is insect myosin or insect myosin components. Said detectably labeled antibody may be labeled with a radiolabel, an enzyme label, a fluorescent label or a chromophore, although an enzyme label is preferred, said enzyme label catalyzing the formation of a visually colored product from an uncolored, differently colored or less colored substrate In greater detail, the present invention involves a method of determining the amount of insect contamination in grain comprising the steps of: 1) preparing an aqueous solution or suspension of a homogenized grain sample; 2) substantially affixing at least a portion of said solution or suspension to a solid surface; 3) applying to said solid surface an antibody-enzyme conjugate, said antibody specifically binding insect antigen and said enzyme catalyzing formation of a colored product from a substrate; 4) washing unbound conjugate from the solid surface; 5) incubating the solid surface with an enzyme substrate under conditions allowing colored product to be formed when enzyme is present; and 6)

correlating amounts of color formed with an amount of insect contamination.

Alternatively, such a detailed method of determining the amount of insect contamination in grain may comprise the steps of: 1) affixing to a solid surface an antibody having specific binding affinity for an insect antigen; 2) preparing an aqueous solution or suspension of a homogenized grain sample; 3) applying at least a portion of said solution or suspension to the solid surface to facilitate binding of any insect antigen to the affixed antibody; 4) washing the solid surface; 4) applying to said solid surface an antibody-enzyme conjugate, said conjugate antibody specifically binding the insect antigen and said enzyme catalyzing formation of a colored product from a substrate; 5) washing unbound conjugate from the solid surface; 6) incubating the solid surface with an enzyme substrate under conditions allowing colored product to be formed when enzyme is present; and 7) correlating amounts of color formed with an amount of insect contamination.

In these methods, the preferred insect antigen is insect myosin or a component thereof; the preferred enzyme is a peroxidase; and the preferred antibody or conjugated antibody may be monoclonal, a mixture of monoclonals or polyclonal.

In one embodiment, the present invention may be described as involving a method of determining the amount of insect contamination in a sample of grain. This particular embodied method comprises the following steps:

1) preparing an aqueous solution or suspension from a homogenized grain sample;

2) contacting a solid surface with said solution or suspension to substantially affix at least a portion of any insect antigen (preferably insect myosin or a component thereof) in said solution or suspension to the solid surface;

3) blocking nonspecific bind sites by incubation of a solution comprising a protein non cross reactive with the antibodies, myosin or its components;

4) incubating said solid surface with a first antibody from a first animal species, said first antibody specifically binding insect antigen;

5) washing unbound first antibody from the solid surface;

6) applying to said washed solid surface a labeled second antibody, said second antibody being from a second animal species, specifically binding the first antibody from the first animal species and said label being a detectable substance which is a fluorescent, radioactive or chromophoric compound or an enzyme (preferably peroxidase) catalyzing formation of a colored product from a substrate;

7) washing unbound labeled second antibody from the solid surface;

8) determining an amount of labeled second antibody bound to said washed solid surface; and 9) correlating the amount of bound labeled second antibody with an amount of insect contamination in said grain, said amount of bound labeled second antibody being proportional to insect antigen in the grain sample.

The most preferred label is an enzyme label and the above method involves (in place of steps 8) and 9)) the steps of:

8a) incubating the solid surface with an enzyme substrate under conditions allowing colored product to be formed when antibody-enzyme conjugate is present; and 9a) correlating amounts of color formed with an amount of insect contamination, said color formation being proportional to the amount of insect antigen present in the grain sample.

In one embodiment, the present invention involves a method of determining the amount of insect contamination in grain which comprises:

1) affixing via chemically or nonspecific binding to a solid surface an antibody having specific binding affinity for an insect antigen;

2) blocking remaining nonspecific binding sites by incubation with a solution comprising a protein non-cross reactive with antibodies or myosin; or, for chemical binding sites, blocking the remaining sites chemically;

3) preparing an aqueous solution or suspension of a homogenized grain sample;

4) applying (possibly after removal of solids) at least a portion of said solution or suspension to the solid surface to facilitate binding of insect antigen to the affixed antibody;

5) washing the solid surface to remove unbound components of the solution or suspension;

6) applying to said solid surface an antibody enzyme conjugate or an antibody conjugated to another label, said conjugate antibody specifically binding the insect antigen and said enzyme catalyzing formation of a colored product from a substrate;

7) washing unbound conjugate from the solid surface;

8) incubating (in the case of an enzyme label) the solid surface with an enzyme substrate under conditions allowing colored product to be formed when the enzyme of the conjugate is present or assaying for the other label; and 9) correlating colored product formed or label present with an amount of insect contamination, the color formation being proportional to amounts of insect antigen in the grain sample.

The antibodies in these procedures may be monoclonal or polyclonal, depending upon the particular specificities desired.

In certain cases the method of the present invention may involve antibodies labeled with a substance such as biotin and a labeled material such as avidin having high affinity for biotin. Such an alternate procedure comprises the steps of:

1) preparing an aqueous solution or suspension from a homogenized grain sample;

2) contacting a solid surface with said solution or suspension to substantially affix at least a portion of any insect antigen in said solution or suspension to the solid surface;

3) blocking nonspecific binding sites by incubation with a solution comprising a protein non-cross reactive with antibodies, myosin or myosin components;

4) incubating said solid surface with biotinylated antibody, said biotinylated antibody specifically binding insect antigen;

5) washing unbound biotinylated antibody from the solid surface;

6) applying to said washed solid surface labeled avidin, said avidin specifically binding the biotinylated antibody and said label being a detectable substance which is a fluorescent, radioactive or chromophoric compound or an enzyme catalyzing formation of a colored product from a substrate;

7) washing unbound labeled avidin from the solid surface;

8) determining an amount of labeled avidin bound to said washed solid surface; and 9) correlating the amount of bound labeled avidin with an amount of insect contamination in said grain, said amount of bound labeled avidin being proportional to insect antigen in the grain sample.

The latter procedure may be favorably modified by first coating the solid surface with a capture antibody necessarily (unless there are multiple, identical or similar, epitopes) having a binding affinity for an epitope of the insect antigen different from the epitope to which the biotinylated antibody binds.

BRIEF DESCRIPTION OF THE DRAWINGS

FIGS. 15A through 15E show an embodiment of the test strip assay of the present invention; FIG. 15A shows dropping of a test solution on the strip; FIG. 15B shows subsequent addition of an antibody enzyme conjugate solution; FIG. 15C illustrates washing the test strip of unbound materials; FIG. 15D shows addition of enzyme substrate to the strip; and 15E illustrates developed color proportional to the amount of insect antigen in the test solution.

FIG. 16A shows test strip immersed in a solution or suspension of test foodstuff; FIG. 16B washed test strip immersed in antibody enzyme conjugate solution; FIG. 16C washed test strip immersed in a solution containing enzyme substrate; and FIG. 16D colored product, visualized on test strip. The enzyme-labeled anti-granary weevil antibody binds to a different myosin epitope than the anti-granary weevil antibody.

DESCRIPTION OF THE PREFERRED EMBODIMENTS

The detection of chitin or insect-specific antigens for determination of insect or insect parts in bulk foodstufs or crops is an object of the present invention.

Insofar as granular foodstuffs such as grain are concerned, immunospecific detection of insect contamination could lead to ready and efficient mechanical cleaning, e.g., by aeration to remove insect pests characteristically dwelling outside grain particles, to produce commercially acceptable bulk grain at reasonable cost.

An efficient method for integrated pest management of growing or mature crops could be developed using the insect detection procedures of the present invention. The specificity of preferred immunoassays could be arranged to detect general insect levels in such crops and to differentiate harmful versus beneficial insect presence. Hence, pesticide use could be minimized and designed to alleviate specific pest problems.

The following Examples relate to preferred specific embodiments of the insect contamination assays of the present invention and are not meant to limit the scope.

EXAMPLE I

Chitin Analysis

Figure 1:
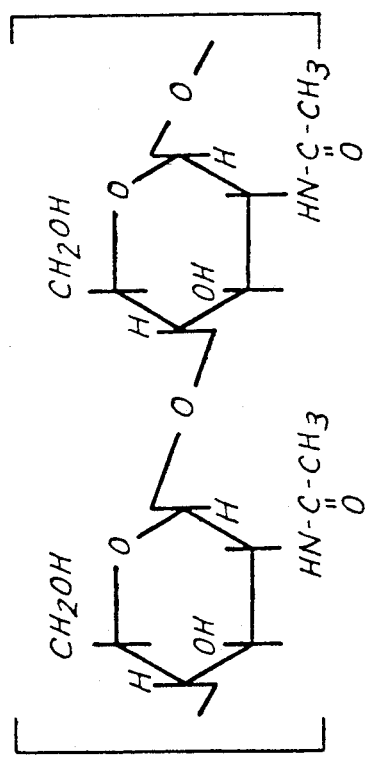
FIG. 1 illustrates the repeating unit of chitin.
Figure 2:
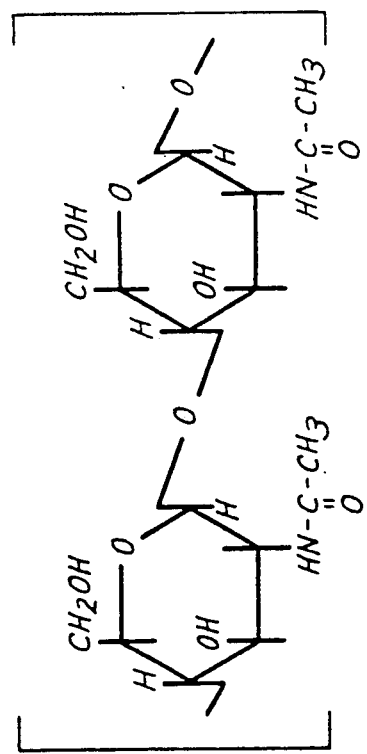
FIG. 2 schematically describes a chitin assay.

A biochemical test for chitin is schematically shown in FIG. 2. Chitin, a beta [1-4] homopolymer of N-acetylglucosamine (NAG), is preferably converted to its monomeric constituent, N-acetylglucosamine, by hydrolysis. This hydrolysis may be induced by enzymes or chemical means, e.g., with acid or alkali. Sensitive assays (e.g., colorimetric) for the N-acetylglucosamine product are available.

It has long been known that certain types of chitin, when subjected to treatment with 0.2% iodine in potassium iodide, followed by treatment with 1% sulfuric acid, develop colored products (17). A more recent modification of this procedure avoids the use of sulfuric acid and gives more uniform color production (18). The test has been used to examine the structural features of chitin in tissues. Such direct color tests for chitin may provide a means for identifying chitin in grains and grain products. One could envision simply crushing grain (or using milled grain) and adding a staining solution, followed by a simple photometric scanning system. These reactions may be adapted for the study of insect contamination.

Several very sensitive methods for N-acetylglucosamine detection have been reported in the literature. The procedure of Reissig, Strominger and Leloir (19) appears to be particularly well suited to the purposes of the present invention and is capable of detecting as little as $3 \times 10^{-10}$ moles of N-acetylglucosamine. Other procedures for NAG assay, such as those of Ride et al. (20) and Tsuji et al. (21) should be usable after appropriate adaptation.

Figure 3:
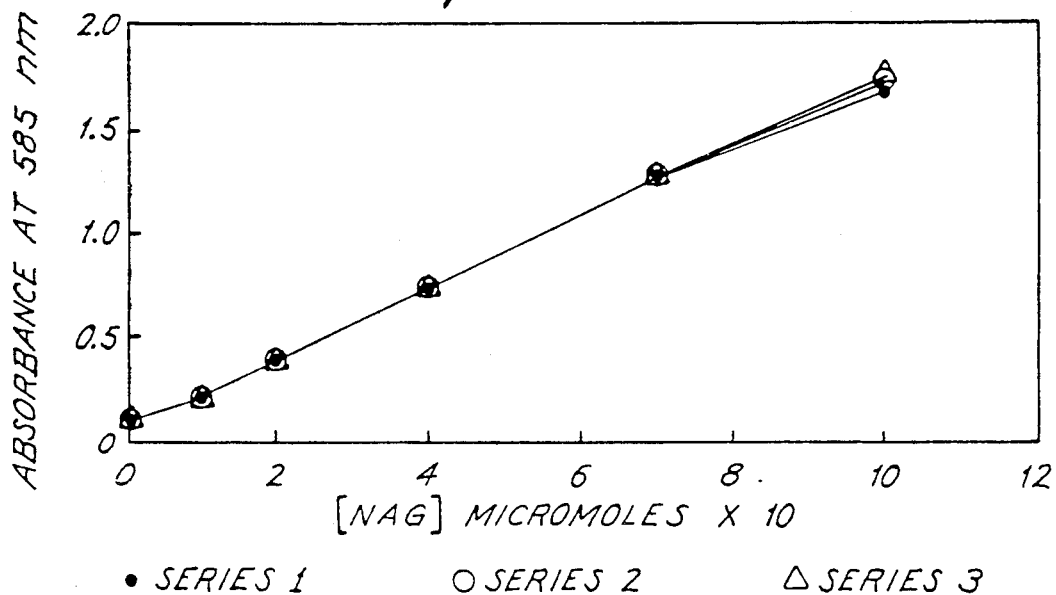
FIG. 3 relates to an NAG standard curve for a chitin assay and illustrates a linear relationship of color development and N-acetylglucosamine concentration in an assay according to Reissig et al. (19).

The NAG assay method of Reissig et al. (19) was tested for sensitivity as follows:

One hundred microliter (ul) of aqueous NAG sample and 20 ul of K (0.8M potassium tetraborate, pH 9.1) were mixed, incubated at 100° C. for 3 minutes and cooled. Six hundred ul of DMAB reagent (1 g dimethylaminobenzaldehyde in 100 ml of analytical reagent grade glacial acetic acid with 12.5% 10N HCl) was added to the cooled mix and this second mixture was incubated at 37° C. for 20 minutes. After cooling to room temperature, the absorbance at 585 nm (nanometer) was measured. FIG. 3 shows the repeatability and linearity of this NAG assay, run at levels expected to be encountered with insect infestation of grain samples.

The conversion of chitin to NAG is a rate-limiting step in preferred available chitin analyses. While acid or alkaline hydrolysis of chitin can be dependable, they generally involve potentially hazardous reagents and may require extensive periods of time. The enzymic hydrolysis of chitin for the purpose of NAG production and assay thereof for insect detection has been accomplished as part of the present invention.

An efficient enzymatic degradation of chitin to N-acetylglucosamine requires the use of two different enzymic hydrolases: chitinase and chitobiase. These chitin-degrading enzymes are present in a wide variety of bacteria and fungi but are difficult to obtain commercially in appropriate quantities and purity. Based on the report of Wadsworth (22), the use of an enzyme preparation from almond emulsions was investigated. This enzyme preparation had been reported to have both chitinase and chitobiase activities. After considerable modification of assay conditions, and using purified chitin as a substrate, it was demonstrated that this new procedure can provide excellent linearity of NAG production over a broad range of chitin concentrations using incubation times as short as 30 minutes.

Under the following conditions, the above enzyme preparation from almond emulsions was used to hydrolyze chitin.

Certain beta-glucosidase preparations were found to have chitobiase activity and that the enzyme preparation available from almonds was contaminated with chitinase. The suitability of the almond extract in hydrolyzing chitin was investigated, and a modification of Reissig's NAG assay (19, 22) was used to quantify the NAG produced.

Method

A glycine/HCl buffer was used in all NAG assays because it was found that citrate buffer interfered with the NAG assay. A glycine/HCl buffer (0.05M, pH 3.5) was found to perform significantly better than a citrate buffer.

An incubation mixture was prepared which contained 1 ml of 0.05M buffer (pH 3.5), 0.5 ml of a 8 mg betaglucosidase/ml buffer (enzyme from almonds, Sigma, No. G0395, lot#38F-4031), 0.5 ml dH$_2$O and 2.5 mg purified grade chitin (Sigma, No. C-3641, lot#107F-7115). The substrate blank (control) contained 1.5 ml of the buffer, 0.5 ml of dH$_2$O, and 2.5 mg chitin. Each incubation mixture was stirred continuously with magnetic stir bars from 30 minutes at RT.

NAG Assay

The incubation mixture was centrifuged at 900 × g for 3 minutes at 4° C. To 0.5 ml supernatant, 0.1 ml of potassium tetraborate was added, and heated in a vigorously boiling water bath for 8 minutes. After cooling with tap water, and adding 3 ml of 1% paraDimethyl-aminobenzaldehyde (DMAB, Aldrich lot#MV 00929LV; 10 g DMAB in 100 ml of 12.5% v/v 10N HCl in analytical grade glacial acetic acid is diluted with 9 volumes reagent grade glacial acetic acid just prior to use). After vortexing and placing in a 37° C. water bath for 20 minutes, then cooling with tap water the absorbance at 585 nm against a distilled water blank was determined (Beckman DU Model 2400). NAG concentration was determined by treating 0.5 ml aliquots of NAG reference solutions ($1 \times 10^{-5}$, $5 \times 10^{-5}$, $1 \times 10^{-4}$, $2 \times 10^{-4}$, $4 \times 10^{-4}$, $1 \times 10^{-3}$M) as above, beginning with the addition of potassium tetraborate.

Results

Ride and Drystale's (20) assay was used to determine the chitin hydrolysis using beta-glucosidase rather than chitinase. After about 35 minutes of incubation, the substrate blank had an average absorbance in excess of 0.850, while the incubation mixture containing the enzyme gave an average absorbance in excess of 1.07. Hence, high absorbances were found after incubation for as little as about 35 minutes, but the solutions containing the beta-glucosidase all had significantly higher absorbances than the substrate blanks (unlike when chitinase alone was used).

In two initial chitinolysis experiments using beta-glucosidase, a practical grade chitin (Sigma, lot#12F-7060) substrate and a Gly/HCl buffer (0.05M, pH 3.5), the absorbance after 30 minutes of incubation was only between 0.02 and 0.04 absorbance units (about $2 \times 10^{-5}$M NAG produced). The control (substrate blanks) gave a 0.00 absorbance reading. With purified grade chitin as the substrate, incubation with beta-glucosidase for 30 minutes gave an absorbance value that exceeded 0.1 units, whereas incubation for 60 minutes gave an absorbance that exceeded 0.2 units. This translated into $7.1 \times 10^{-5}$M and $1.4 \times 10^{-4}$M NAG produced, respectively. Hence, beta-glucosidase catalyzed chitinolysis of practical grade chitin, as was expected.

In a later assay, beta-glucosidase was incubated with purified grade chitin for times of 0.5 hours, 1.5 hours, 19.17 hours, and 24 hours. Absorbance value ranged from ca. 0.206 for the 0.5 hour incubation to over 1.03 for the 24 hour incubation ($1.14 \times 10^{-4}$M NAG and $5.74 \times 10^{-4}$M NAG, respectively). In another assay, it was found that a 0.5 hour incubation gave an absorbance of 0.172 and that the 24 hour incubation yielded 1.06, corresponding to $8.05 \times 10^{-5}$M and $5.73 \times 10^{-4}$M NAG, respectively. The following observations were also made:

1. The NAG assay shows a linear relationship (correlation coefficient, r, is greater than 0.99) between absorbance and [NAG] for concentrations less than or equal to $2 \times 10^{-4}$M. Significant "flattening" occurs after [NAG]=$4 \times 10^{-4}$M.

2. NAG reference solution are preferably used each time an assay is run because final absorbances may vary slightly.

3. The control (substrate blank) for the hydrolysis of chitin from Sigma (purified or practical) gives a significantly lower absorbance (less than 1/10th) than the solution containing the beta-glucosidase with the chitin.

4. The Beckman DU Model 2400 Spectrophotometer gave dependable absorbance readings.

Figure 4:
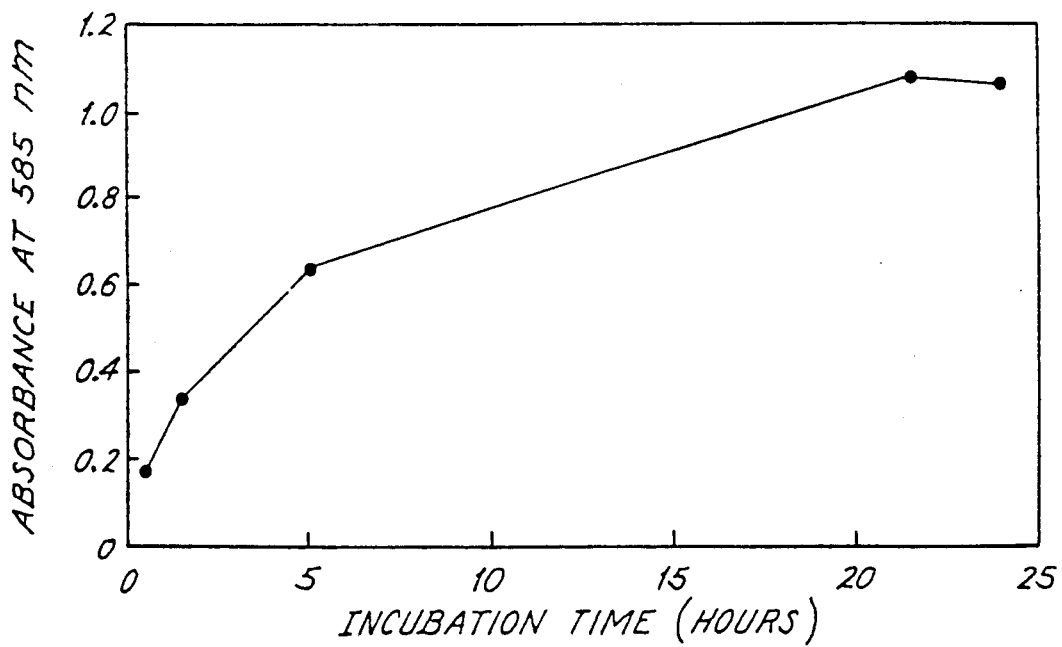
FIG. 4 relates to an enzymatic assay chitin assay system and shows the hydrolysis of chitin to NAG by enzymes from an almond emulsion.

Free NAG produced at various periods of time was colorimetrically determined by the method of Reissig et al. (19) adapted for the present purpose. One hundred microliters (ul) of aqueous NAG sample and 20 ul of $K_3BO_3$ (0.8M potassium tetraborate, pH 9.1) were mixed, incubated at 100° C. for 3 minutes and cooled. Six hundred ul of DMAB reagent (1g dimethylaminobenzaldehyde in 100 ml of analytical reagent grade glacial acetic acid with 12.5% 10N HCl) was added to the cooled mix and this second mixture was incubated at 37° C. for 20 minutes. After cooling to room temperature, the absorbance at 585 nm (nanometers) was measured. Data from the enzyme hydrolysis technique are shown in FIG. 4, which depicts the amount of NAG-dependent color developed upon colorimetric assay as described above when chitin-containing samples are incubated with enzymes for varying times. Note that a readily measured amount of color (0.17 absorbance units) was produced even when the enzymatic hydrolysis was carried out for only a 30 minute incubation time. The enzyme hydrolysis procedure provides an assay which is of comparable sensitivity to the chemical methods and promises to reduce the time required for accurate analyses.

The experiments described above were carried out using a dual enzyme system consisting of both chitinase and chitobiase from almonds. These results showed both a rapid and linear release of N-acetyl glucosamine from purified crab shell chitin. Readily detectable amounts of N-acetyl glucosamine were produced with as little as 15 minutes incubation of the enzymes with the chitin substrate.

Subsequent experiments were carried out using the granary weevil Sitophilus oranarius as the source of chitin. Whole weevils were frozen in liquid nitrogen in a test-tube and crushed to a powder with a pestle. Glycine/HCl buffer (0.05M, pH 3.5) was then added to yield a final concentration of 2.5 mg weevil/ml. Aliquots of this suspension were then subjected to chitinase/chitobiase hydrolysis. The amount of N-acetyl glucosamine released was shown to be proportional both to the amount of insect material added and to the period of incubation. However, the degree of hydrolysis was consistently considerably less than was observed with purified crab shell chitin. Possible reasons for these results include the presence of proteases in the ground insects which would diminish the activity of the chitinolytic enzymes; the presence of enzyme inhibitors in the extract or a need for the insect chitin to be processed further to generate a more suitable substrate for the enzymatic hydrolysis.

It is thus feasible for the degree of contamination by insects or insect parts to be detected in foodstuffs such as whole or milled grain by the direct or indirect assay of chitin.

EXAMPLE 2

Immunological Test System

Immunological assay procedures offer an exceptionally sensitive means for detecting biological compounds. The clinical assays for human chorionic gonadotropin, available as over the counter pregnancy tests, as well as assays for pesticide residues and for mycotoxins such as aflatoxin demonstrate the utility of this approach. In the most preferred immunological assay procedures of the present invent, an insect protein antigen is utilized. The muscle protein myosin, the most preferred insect antigen, is present in relatively large quantities in all life stages of insects and is found in insect remains as well. Myosin is a slowly evolving protein, so that antisera prepared against this protein cross-reacts with the myosins of other insect species.

Figure 5A:
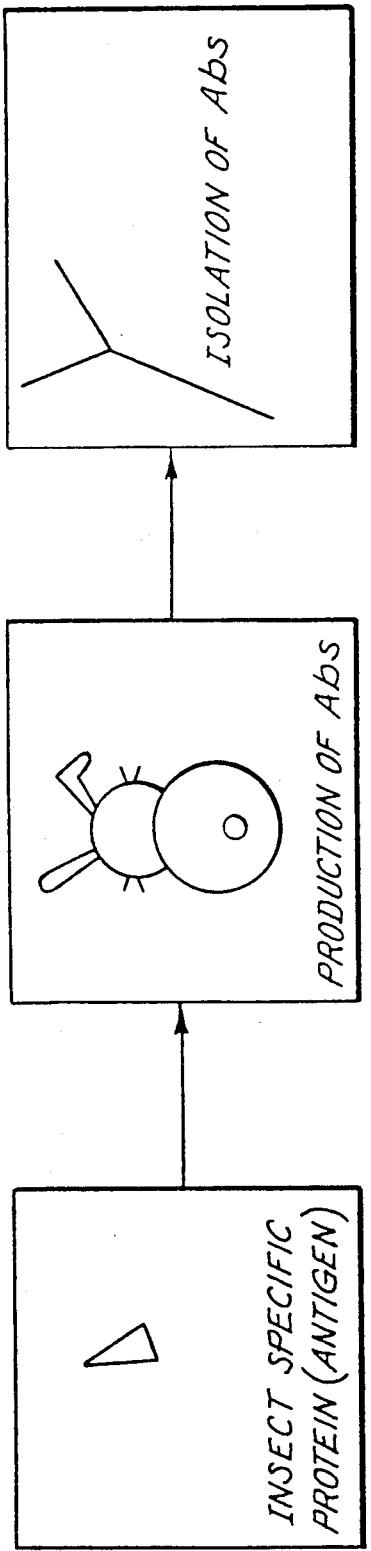
FIGS. 5A and 5B describe an outline of procedures in the development of an insect-specific immunoassay.
Figure 5B:
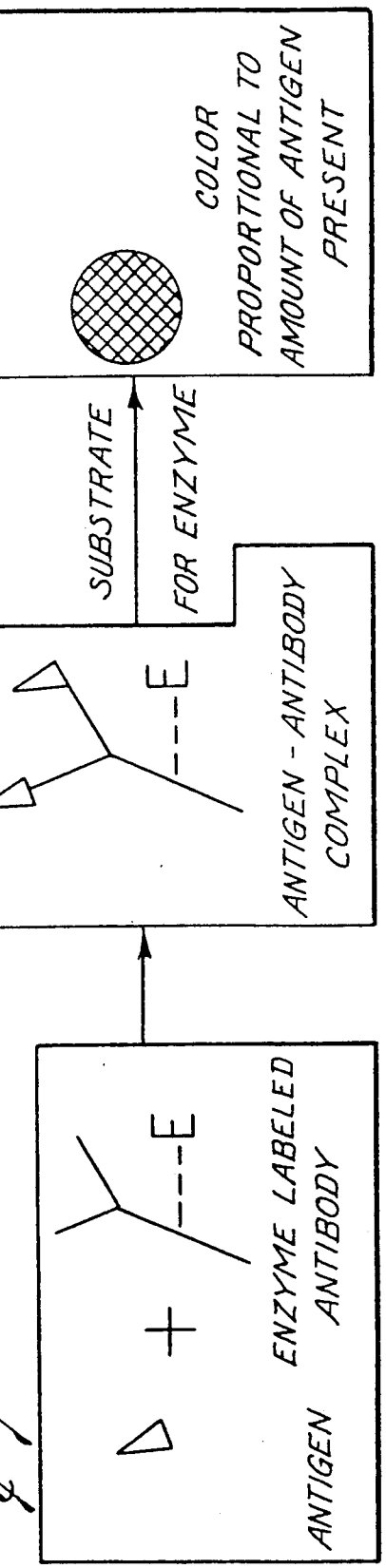

An outline of the procedures used to develop a laboratory-style immunological assay for insect materials is given in FIG. 5. Initial studies were carried out using cricket myosin. Using antibodies obtained against cricket myosin and its components in rabbits, an ELISA (enzyme linked immunosorbent assay) was developed. It was demonstrated that this type of assay had excellent sensitivity and the potential for determining cross-reactivities with a wide variety of grain insects.

The experiments and results detailed herein establish a proof of principle test system for the development of an immunological assay to detect insect specific protein contaminating whole and milled grain. Using antibodies against an insect myosin as different from grain pest myosin as cricket myosin, a substantial cross-reaction with crude extracts from a broad range of the most common insect pests of stored grain was demonstrated. If it is assumed the average grain pest weighs approximately 2.5 mg, and that 1% of this weight is myosin (i.e., $2.5 \times 10^{-5}$ g of myosin), then the average grain pest contains at least 1,250 times the myosin necessary to give a positive test result in the myosin ELISA described here. The assay was also shown to be linear over a broad range of antigen concentration. It should be noted that the detection limit and linear response range of the assay are most likely limited by the protein absorptive capacity and characteristics of the polystyrene microtiter plates.

The adaptation of this laboratory-based assay to a reagent strip ("dip-stick") format is currently being developed. "Dip Stick" ELISA's are easy to perform, rapid, and inexpensive. Successful adaption of the myosin ELISA to this reagent strip format would allow relatively untrained workers to test for insect contamination of whole and milled grain at granaries, for example. Early work has focused on the enzyme linked immunospot (ELISPOT) assay reviewed by Monroe (33). The ELISPOT assay is essentially an ELISA performed on nitrocellulose, which has a much greater protein absorptive capacity than polystyrene. Preliminary results indicate the myosin ELISPOT is at least 30 times more sensitive than the myosin ELISA. Here, the average grain pest would have over 50,000 times the myosin needed to give a positive test.

As encouraging as these results with antibodies to cricket myosin have been, an ELISA using antibodies directed against the myosin of a grain pest may offer certain improvements. The present inventors have recently extracted myosin from *Sitophilus granarius* (granary weevil), and used it to produce polyclonal antibodies. These antibodies showed broad cross-reaction with crude extracts from a wide variety of other grain pests. Development of a dipstick assay based on these antibodies is also currently in progress.

Monoclonal antibodies to granary weevil myosin will be prepared by the usual methods well-known in this area. Monoclonal antibodies should allow even more quantitative ELISA and ELISPOT assays to be developed, and will provide an almost unlimited source of antibodies specific for the same antigenic determinants (epitopes). This will allow more ready standardization of the assay, which is important in the development of an optimal assay for use in the field. Once a standardized assay has been developed, it may be automated and incorporated for the detection of insect contamination of grain into procedures already in use at granaries for testing grain hardness and moisture content. Finally, further development of the monoclonal antibody test might also allow not only quantitation of insect infestation, but identification of the species of infesting insect.

EXAMPLE 3

Materials and Methods Involved in an Immunoassay

Figure 6:
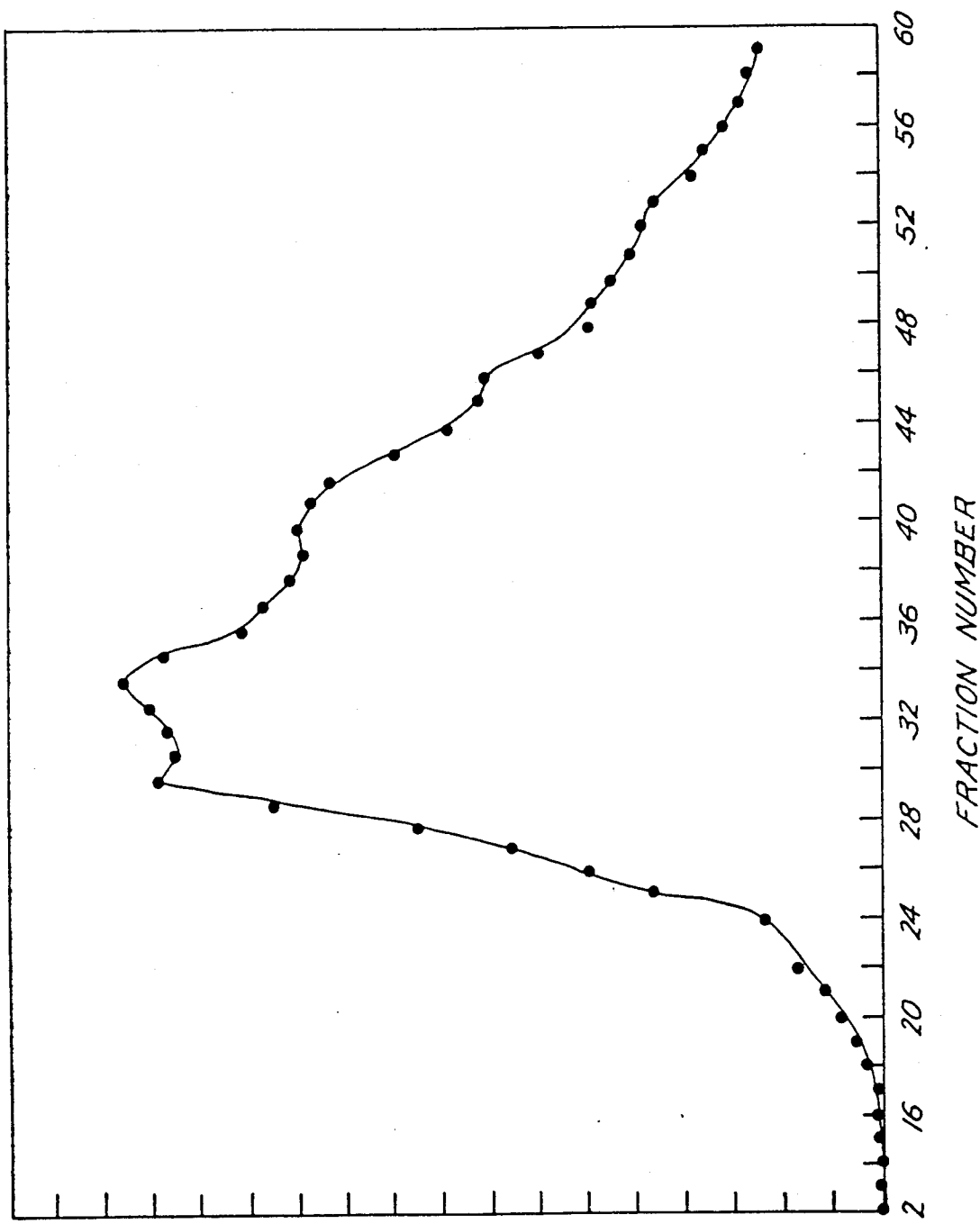
FIG. 6 shows the elution profile (relative light absorption) of crude cricket myosin from Sephacryl S-300 gel filtration column.

The myosin extraction procedure used was an adaptation of those used by Chaplain (23) and Woods (24). Crickets were obtained live from the American Angler Tackle Center (Austin, Tex.) and kept at $-20°$ until used. Upper rear leg segments were removed from 150 crickets, and homogenized in a Waring Commercial blender with enough 0.3M sucrose/20 mM Tris-Cl/1 mM EDTA (pH 7.2) to create a semi-thick slurry. Structural residue was removed by centrifugation at 2500 rpm (SS-34 rotor) for 20 min. The pellet was then extracted with stirring in ten times its volume of 0.7M KCl/20 mM Tris-Cl(pH 7.8) for 6 hrs. at 4° C. After centrifugation at 8,000 rpm for 25 min., the supernatant was carefully removed. Actomyosin was precipitated by dilution of the supernatant to an ionic strength of 0.05 using deionized $H_2O$, resuspended in a minimal amount of 0.6M KCl/5 mM $MgCl_2$(pH 8.0 with $NaHCO_3$), shaken, and centrifuged at 36,000 rpm (type 40 rotor) for 2 hrs. The supernatant was then dialyzed overnight at 4° C. against 0.05M NaCl. Afterwards, the precipitate was removed by centrifugation at 10,000 rpm (SS-34 rotor) for 20 min., and the pellet resuspended in enough 0.5M NaCl to give a solution with an absorbance at 280 nm of 3.0 (determined using a Beckman DU-50 spectrophotometer). A Sephacryl S-300 (Pharmacia) gel filtration column was packed (1.5 cm$\times$69 cm) and equilibrated with 0.5M NaCl at a flow rate of 0.8 ml/min. A 0.5 sample was loaded on to the column and 2 ml fractions were collected. Protein elution was followed by monitoring the absorbance of the fractions at 280 nm. Fractions corresponding to peaks were then frozen at $-20°$ C. (the elution pattern is shown in FIG. 6). Myosin pellets were also purified using the ammonium sulfate precipitation procedure of Wang et al. (25). After the precipitate was resuspended and dialyzed as above, the final solution was stored under liquid $N_2$.

Myosin purity was then evaluated using sodium dodecylsulfate polyacrylamide gel electrophoresis (SDS-PAGE). The method used was a modification of the procedures of Weber and Osborn (26), and is detailed in the SIGMA Chemical Company Technical Bulletin No. MWS-877 (1986). Myosin pellets were resuspended in 0.5M NaCl at an approximate protein concentration of 3 mg/ml, as determined by the method of Bradford (27). Fractions from the S-300 column were also analyzed using SDS-PAGE, and were combined as is with sample buffer. Analytical runs on 5% gels were performed with 20-25 ug of total protein; preparative gels were run with 50 ug of total protein. Gels were stained overnight in 25% isopropanol/10% acetic acid/0.1% Coomassie Blue R-250/ and 0.1% cupric acetate in deionized $H_2O$, and destained in 10% ethanol/10% acetic acid in deionized $H_2O$ until the background staining reached an acceptable level. The gels were scanned using a GS-300 densitometer (Hoefer Scientific Instruments, San Francisco, Calif.) at 585 nm. Final protein concentrations per band were then calculated by cutting out the band peaks, weighing them, and correlating this to the total protein concentration.

Protein bands corresponding to myosin heavy chain were excised from the gels, diced with a single edged razor, and ground in a tissue grinder in 0.15M NaCl following an adaptation of the procedure of Hunter et al. (28). The final mixture, containing approximately 100 ug (microgram) of myosin heavy chain/ml, was stored at $-20°$ C. until used. Antibodies to the denatured heavy chain of myosin were raised in 4 month old male New Zealand white rabbits using an adaptation of the procedures of Hurn and Chantler (29). For primary immunization, 0.5 ml of myosin gel mixture (50 ug of myosin heavy chain) was suspended in 0.5 ml Freund's complete adjuvant (Colorado Serum Co., Denver, Colo.), and injected subcutaneously in multiple sites on the hind quarters of the rabbit. Booster injections were given at approximately one month intervals after primary immunization, and consisted of 50 ug myosin heavy chain gel mixture (first and second boosts), or 60 ug gel mixture (third and fourth boosts), suspended in 0.15M NaCl and injected subcutaneously in multiple sites. Total volume for all booster injections never exceeded 1.5 ml. Blood was drawn from a marginal ear vein 10 days later, and allowed to clot overnight at room temperature. The next day, the clot was removed and the serum stored at $-20°$ C.

Enzyme linked immunosorbent assay (ELISA) was performed using an adaptation of the procedure of Browning et al. (30). Microtiter wells were coated with 50 ug of the antigen solution. Antigens were usually dissolved in 0.5M NaCl. Rabbit antiserum was always diluted in buffer HNAT (10 mM Hepes-KOH, pH 7.6, 0.2% bovine serum albumin, 0.02% Tween 80) and 50 ug of first antibody was added to each well. Blank wells were prepared using rabbit preimmune sera. The second antibody was goat anti-rabbit IgG conjugated to horseradish peroxidase (Kirkegaard and Perry Laboratories). Incubations with antigen and antibodies, as well as blocking incubations, were all for 30 min. After addition of the reaction mixture, the microtiter plates were incubated for 20 min. at room temperature, and the reaction stopped by the addition of 0.1 ml 0.01% NaN₃ to each well. The absorbance was then measured either at 405 nm using a Bio-Tek Instruments Model EL310 EIA plate reader or at 414 nm using a BIORAD EIA plate reader model 2510.

Crude extracts of grain pests were prepared by taking 100 mg of the dead insect (stored at −80° C.) and grinding them up in 2 ml of 0.5 M NaCl. The resulting mixture was then centrifuged at 5000 rpm (SS-34 rotor) for 20 min. and the supernatant stored under liquid $N_2$ until tested.

EXAMPLE 4

Immunoassay Development

Myosin was extracted from thigh muscles of the common cricket following procedures detailed in Example 2 and 3. The crude myosin preparation was further purified on a Sephacryl (Pharmacia) S-300 gel filtration column, and the elution profile of this column is shown in FIG. 6. SDS-polyacrylamide gel electrophoresis of the crude myosin and fractions from the S-300 column was performed. After SDS-PAGE, the major bands in the crude myosin gel corresponded to myosin heavy chain (200 kD) and what may be a paramyosin subunit (105 kD). Paramyosin is a muscle protein limited in distribution to the invertebrates and forms a core in the thick filaments around which myosin wraps (31). Minor bands correspond to actin (ca. 43 kD), tropomyosin (ca. 28 kD) and myosin light chain (ca. 18 kD). As seen from S-300 column fraction PAGE gels, column gel filtration removed lower molecular weight contaminants from the crude myosin preparation. However, the apparent paramyosin was still present. Resuspended crude myosin pellets were also purified following the ammonium sulfate precipitation procedure of Wang et al. (32). SDS-polyacrylamide gels of a myosin preparation before and after the salt fractionation showed that a substantial amount of paramyosin contamination remained even after ammonium sulfate precipitation, although lower molecular weight contaminants were removed.

Antibodies directed against cricket myosin heavy chain were obtained by initially immunizing male New Zealand white rabbits with cricket myosin heavy chain bands excised from polyacrylamide gels of the S-300 column fractions. Crude cricket myosin could also be used as an immunogen to generate appropriate antibodies. Booster injections were prepared using myosin heavy chain bands from gels of ammonium sulfate precipitation purified myosin. These antibodies were then used to develop an enzyme linked immunosorbent assay (ELISA) for cricket myosin. Some details of ELISA procedures are given in Example 1. The ELISA procedure was adapted from that of Bahr et al. (34) and may be more fully described as follows. Fifty ul of antigen solution or sample was added to a microtiter well and the microtiter plate was incubated at room temperature (RT) for 30 minutes. Excess antigen or sample was removed by a single washing with buffer HN (10 mM HEPES/KOH pH 7.6, 150 mM NaCl). One hundred ul of buffer HNA (buffer HN with 1% bovine serum albumin (BSA)) was then added to each well, followed by a 30 min incubation at RT. Buffer HNA was removed and each well washed twice with buffer HNAT (buffer HN with 0.2% BSA and 0.02% TWEEN 80). Fifty ul of an antibody solution appropriately diluted in buffer HNAT (the antibody being specific for insect myosin or a component thereof) was added to each well and incubated for 30 min at RT. The antibody solution was removed and each well washed thrice with buffer HNAT. Fifty ul of a solution comprising goat antibody specific for rabbit IgG and conjugated to horseradish peroxidase was then added to each washed well. After a 30 min incubation at RT, unbound goat antibody conjugate was removed and each well washed thrice with buffer HNAT. A reaction mixture was prepared by mixing 50 ul ABTS (70 mg 2,2'-azino-bis-3-ethylbenzthiazoline sulfonic acid (Sigma); 5 ul 30% $H_2O_2$ and 4.95 ml of 0.1M sodium citrate-citric acid, pH 4.2. One hundred ul of reaction mix was added to each well and incubated (preferably for 10-20 minutes). If the microtiter plate is to be scored for developed color on a spectrophotometer, color development is stopped by addition of 100 ul of stopping reagent ($1.82 \times 10^{-3}$M NaN₃) and the color produced measured spectrophotometrically at 414 nm.

Figure 7:
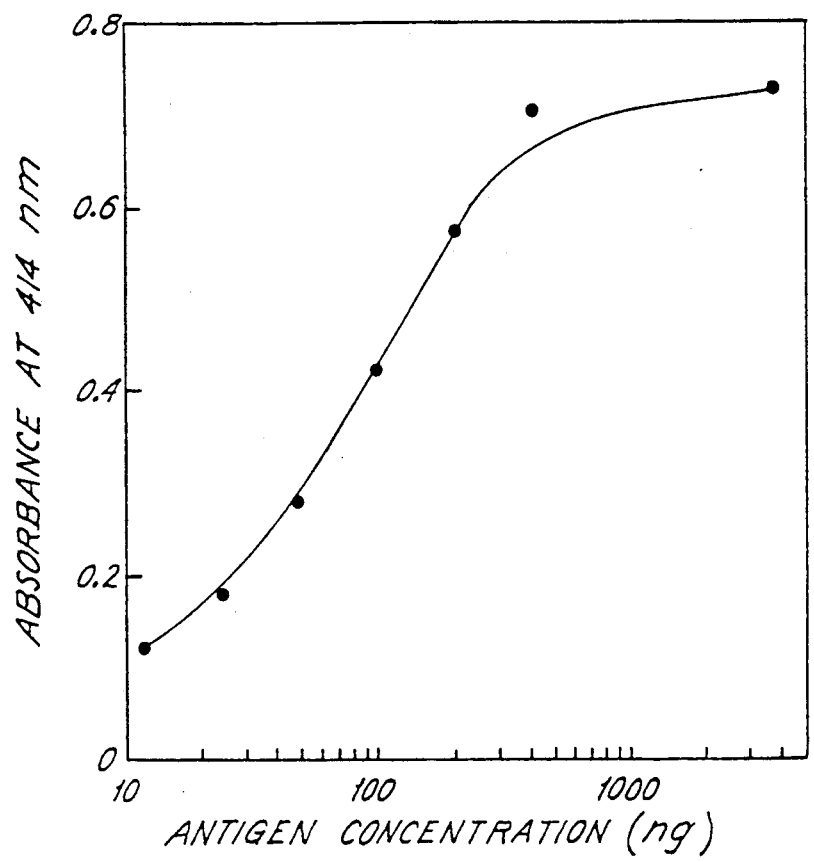
FIG. 7 relates to the sensitivity of the myosin ELISA and shows a cricket myosin ELISA at various myosin concentrations.
Figure 8:
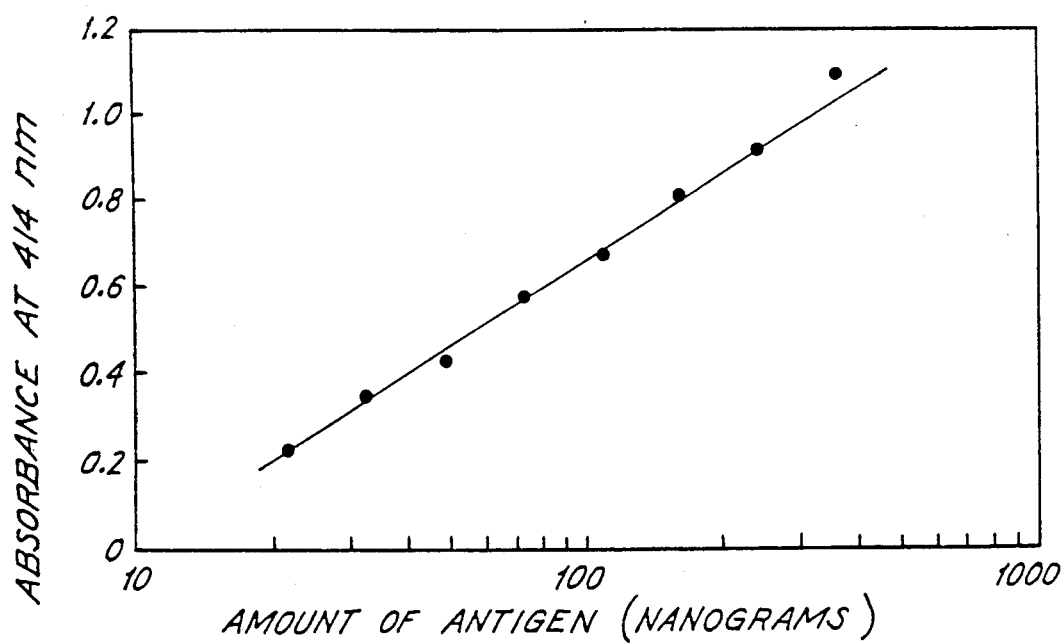
FIG. 8 shows the linearity and range of the cricket myosin ELISA.

The sensitivity of the myosin ELISA was evaluated by testing the ability of the ELISA to detect myosin in dilutions of a crude cricket myosin solution. FIG. 7 is a plot of the response of the myosin ELISA as a function of antigen concentration, and shows that the myosin ELISA can easily detect low (nanogram) quantities of crude myosin. The leveling of the assay response at higher total protein concentrations can be attributed to reaching the protein absorptive capacity of the polystyrene wells in the microtiter plates. The linear range of the myosin ELISA was also determined, and is shown in FIG. 8. The assay's linear response easily spanned a ten-fold total protein concentration range (22ng-380 ng), and demonstrated usability as a quantitative assay for insect myosin.

The ability of the cricket myosin-based ELISA to detect myosin in crude extracts of a wide variety of common grain pests was evaluated, and the results are reported in Table 1. The cricket myosin ELISA had a strong cross reaction with crude extracts of this broad range of the most common and serious pests of stored grain. This shows that the cricket myosin-ELISA can detect myosin in all of the grain pests tested and affirms that a cricket myosin-based ELISA may be used for detecting a wide variety of insect pests contaminating foodstuffs such as whole and milled grain.

TABLE 1

| GRAIN PESTS WHOSE CRUDE EXTRACTS WERE DETECTABLE USING A CRICKET MYOSIN-BASED ELISA | |
|---|---|
| Grain Pest | Assay Response (O.D. at 405 nm) |
| Sitophilus zeamais (maize weevil) | 0.18 |
| Sitophilus granarius (granary weevil) | 0.40 |
| Sitophilus oryzae (rice weevil) | 0.28 |
| Trogoderma variabile (warehouse beetle) | 0.78 |
| Trogoderma glabrum | 0.80 |
| Tribolium castaneum (red flour beetle) | 0.78 |
| Tribolium confusum (confused flour beetle) | 0.39 |
| Oryzaephilus mercator (merchant grain beetle) | 0.89 |
| Rhyzopertha dominica (lesser grain borer) | 0.29 |
| Prostephanus truncatus (larger grain borer) | 0.75 |
| Lasioderma serricorne (cigarette beetle) | 0.39 |
| Stegobium paniceum (drugstore beetle) | 0.22 |
| Callosobruchus maculatus (cowpea weevil) | 0.76 |
| Attagenus megatoma (black carpet beetle) | 0.58 |

TABLE 1-continued

GRAIN PESTS WHOSE CRUDE EXTRACTS WERE
DETECTABLE USING A CRICKET
MYOSIN-BASED ELISA

| Grain Pest | Assay Response (O.D at 405 nm) |
|---|---|
| 1:500 dilution of crude cricket myosin | 0.42 |

EXAMPLE 5

Granary Weevil Myosin Immunoassay

Granary Weevils were obtained from the U.S. Department of Agriculture Research Service, Department of Entomology, University of Wisconsin, Madison, Wis. 53706. Antisera to crude granary weevil myosin were prepared by a procedure analogous to that of Example 2. An ELISA assay analogous to that described above for cricket myosin was developed. Table 2 shows a variety of insects detectable using this granary weevil myosin-based ELISA.

TABLE 2

Grain Pests Detectable Using an
Anti-granary weevil Myosin ELISA

*Sitophilus zeamais* (maize weevil)
*Sitophilus oryzae* (rice weevil)
*Trogoderma variabile* (warehouse beetle)
*Trogoderma glabrum*
*Tribolium castaneum* (red flour beetle)
*Tribolium confusum* (confused flour beetle)
*Oryzaephilus mercator* (merchant grain beetle)
*Rhyzopertha dominica* (lesser grain borer)
*Prostephanus truncatus* (larger grain borer)
*Lasioderma serricorne* (cigarette beetle)
*Stegobium paniceum* (drugstore beetle)
*Callosobruchus maculatus* (cowpea weevil)
*Attagenus megatoma* (black carpet beetle)
*Alphitobius diaperinus* (lesser mealworm)
*Plodia interpunctella* (indian mealworm)

Figure 9:
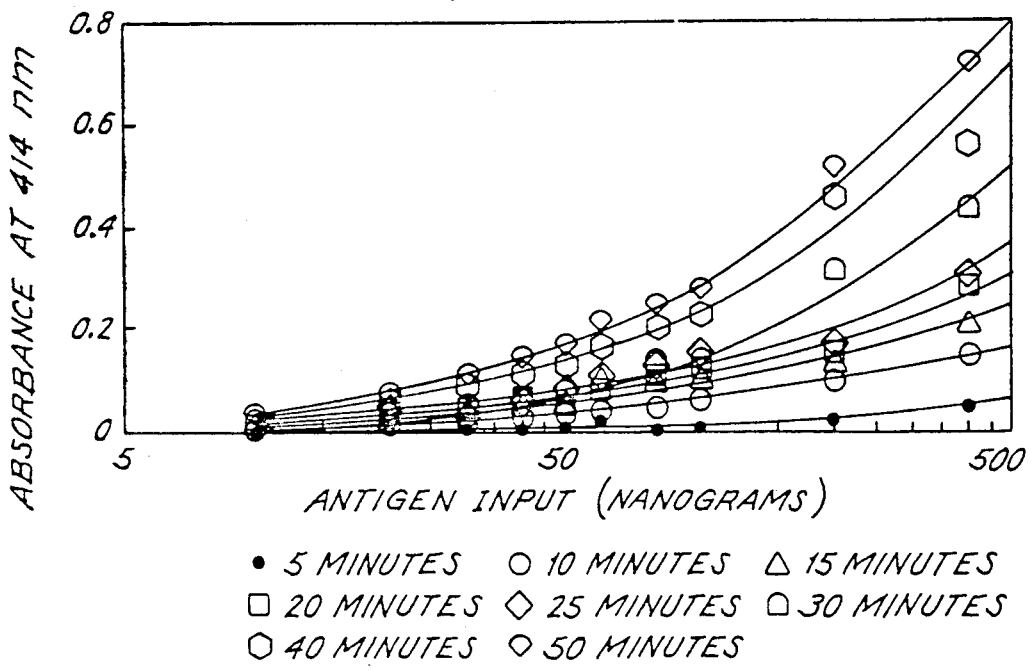
FIG. 9 shows the effects of reaction time variation (time increments) on the granary weevil ELISA.
Figure 10:
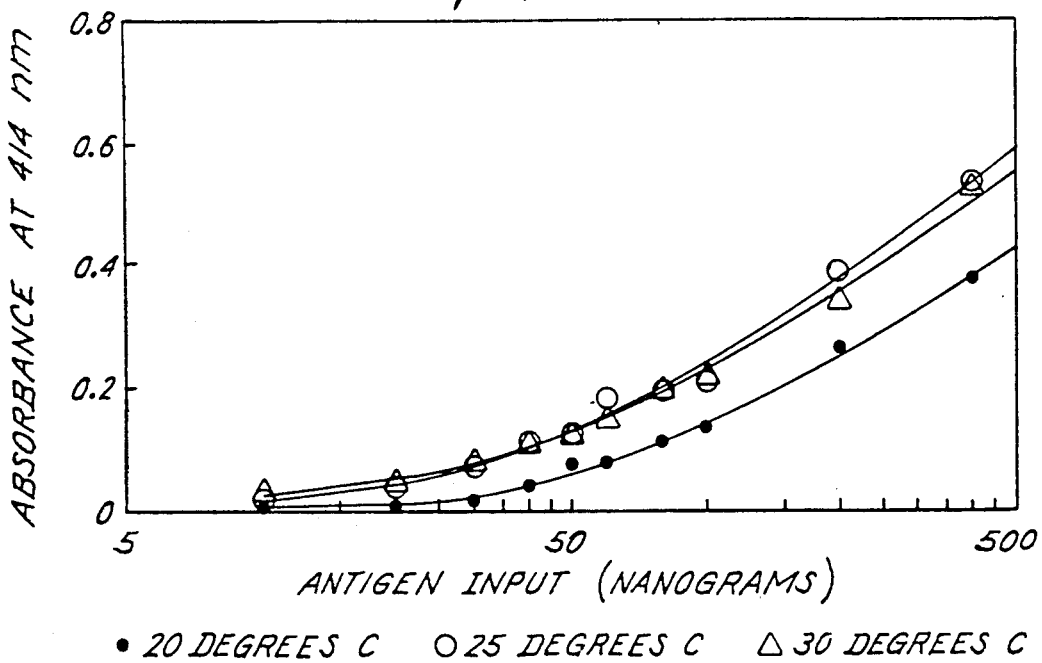
FIG. 10 illustrates the effects of temperature on the granary weevil ELISA for immunological detection of insects.

A number of parameters of the granary weevil myosin ELISA system were examined to be sure the assay procedure operated at optimal sensitivity and also provided data within a short period of time. The effect of varying reaction times for the assay is shown in FIG. 9. Using a 96-well microtiter plate system it was found that a minimum of approximately 15 minutes of incubation time was appropriate for this type of assay. More rapid immunoassays, for example, using a test-strip type assay described elsewhere herein, may be developed. The effect of temperature on the assay procedure is illustrated in FIG. 10. While the assay is indeed affected by temperature, the effect is not large and the small changes in the assay observed with varying temperature can readily be adjusted by including control samples in the assay system. It is important to note that the assay procedure is relatively insensitive to temperature in the normal range of operating conditions.

Figure 11:
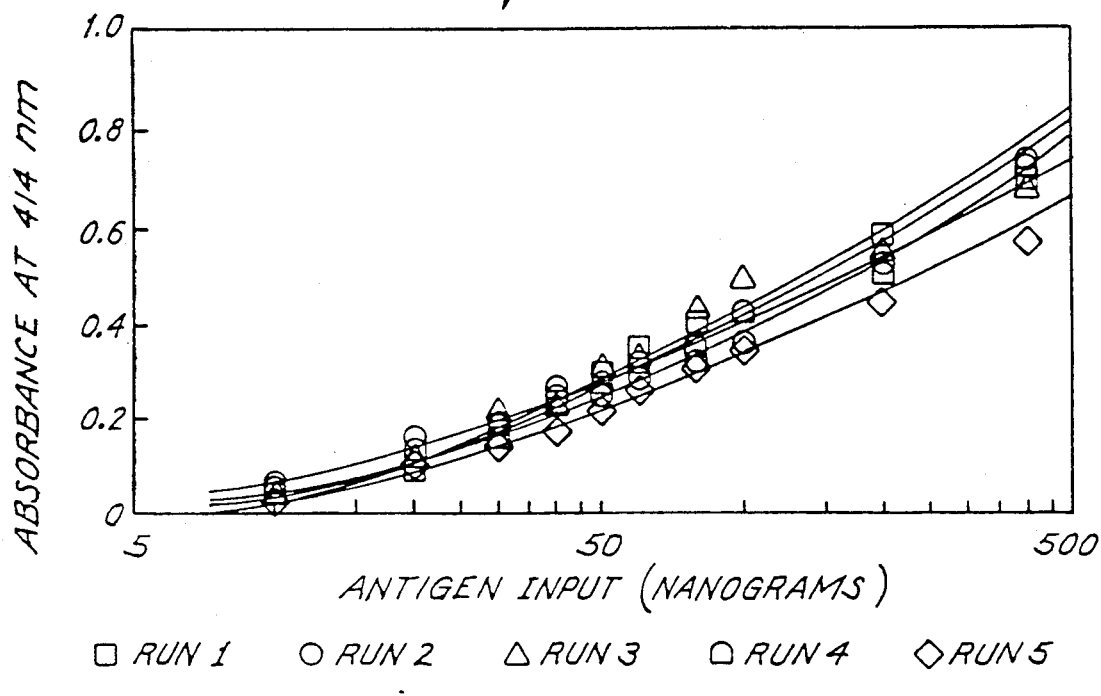
FIG. 11 shows reproducibility of the granary weevil ELISA on successive days for the immunological detection of insects.
Figure 12:
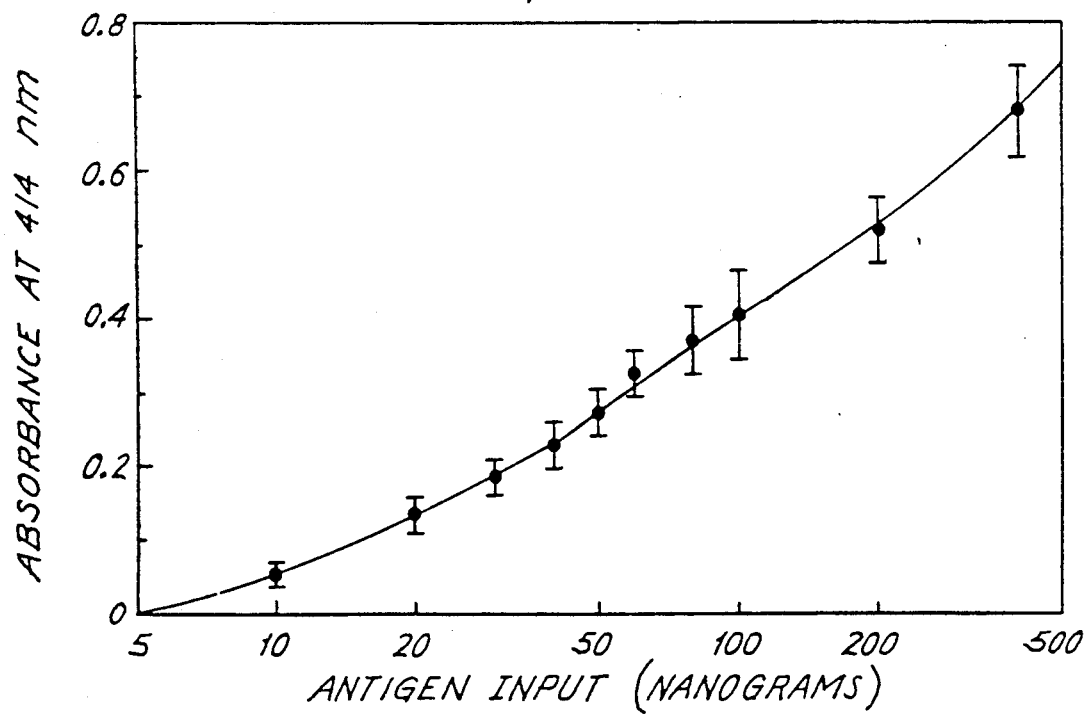
FIG. 12 illustrates the statistical reproducibility of the granary weevil ELISA (data from 5 plates run on different days).

Another concern was that any assay procedure for detecting insect contamination has to be highly reproducible. Data from several successive days of testing using the *Sitophilus granarius* (grain weevil) antibody system are shown in FIGS. 11 and 12. In the FIG. 12, the error bars represent one standard deviation on either side of the average value. These data represent a collection of standard curves and the standard curves differ very little from day to day. It is anticipated that, for optimal accuracy, standards would be run each day when actual tests for contamination are being carried out.

Figure 13:
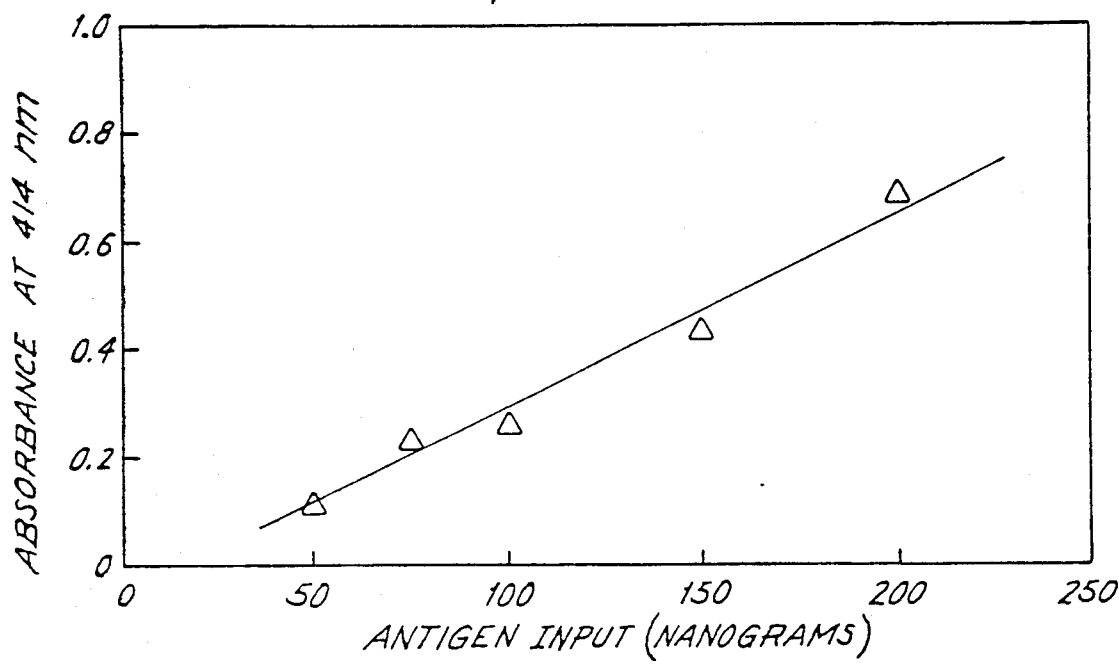
FIG. 13 describes the sensitivity of a granary weevil myosin ELISA assay in the presence of flour.

It was necessary to establish that such immunological assays functioned properly in the presence of ground grain. Assays for live or dead insect remains in whole kernels will require grinding the grain and extracting the myosin or components of myosin. A similar extraction procedure is required for milled grain. A preliminary set of data obtained for myosin admixed with flour is presented in FIG. 13. Although some background absorption was noted in these experiments, the requisite sensitivity for insect myosin was otherwise not substantially changed.

Figure 14:
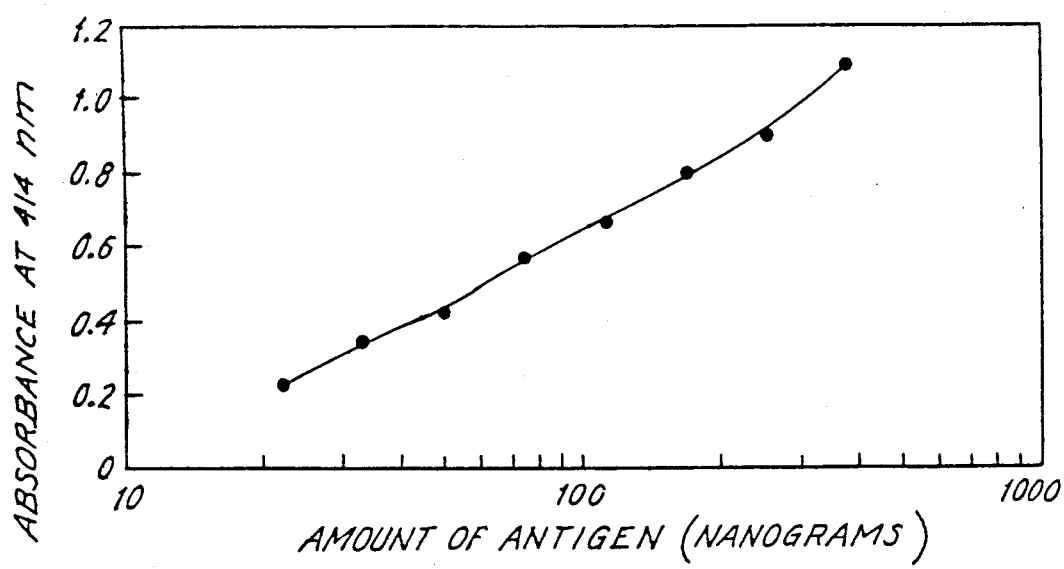
FIG. 14 shows the sensitivity of a granary weevil myosin ELISA.
Figure 16A:
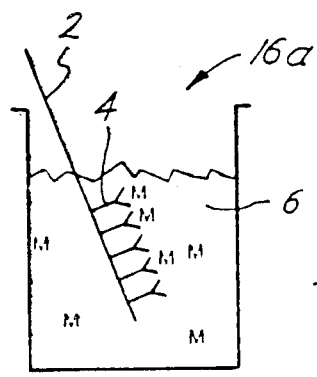
FIGS. 16A through 16D show a second embodiment of the test strip assay of the present invention.
Figure 16B:
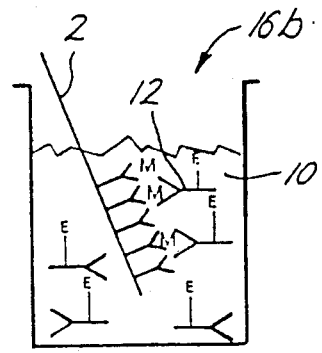
Figure 16C:
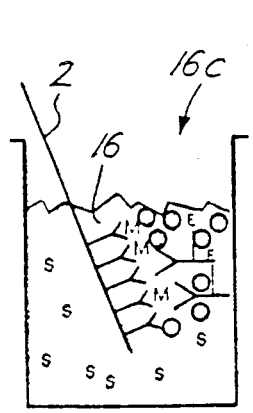
Figure 16D:
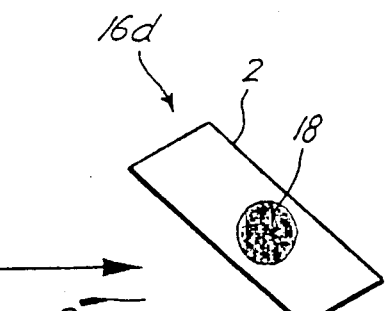

The sensitivity of the granary weevil ELISA system is illustrated in FIG. 14. Clearly, such an immunological test provides both linearity over a broad range of myosin concentrations and has the requisite degree of sensitivity. In this type of assay it is estimated that a level of contamination of one insect per 1,000 grams of grain would be equivalent to approximately 90 nanograms of antigen. Tests have also established that such an ELISA assay can be extended in sensitivity by at least about five fold.

These results indicate that the assay is: 1) sufficiently sensitive; 2) the assay detects a broad range of insects; and 3) may be adapted to a rapid, inexpensive, and easy-to-use format.

EXAMPLE 6

Development of a Test Strip Assay

For purposes of field use, a convenient system of immunoassay may be readily developed. For example, as shown in FIGS. 15A-15E a test strip would have a substantially colorless area for receipt of a drop of test solution. The test solution would be an aqueous extract or suspension of, for example, a homogenized grain sample. A portion of this aqueous extract would then be applied to the test strips. The test strip would then be dried to enhance affixation of any insect antigen present. Subsequently, an antibody conjugated with a label such as an enzymic label would be added to the test strip. After washing unbound antibody conjugate away, a substrate solution for the enzyme would be added and color development observed. The extent of color development would be proportional to the amount of insect antigen (such as myosin or components thereof) present in the test solution.

FIGS. 16A-16D represent a more generally accepted model for such a test strip assay. In this model, the test strip 2 would contain a substantially white center of a substance such as nitrocellulose (e.g., Immobilon) which has been treated to bind an immunoglobulin 4 having specific affinity for an insect antigen such as myosin (M). The test strip would be characteristically blocked for nonspecific absorption and dipped in an aqueous solution or suspension 6 in which a grain sample has been homogenized. This would allow any antigen (M) present in the aqueous solution or suspension 6 to bind to the antibody 4 on the test strip 2. After washing 8 unbound material from the test strip 2, the test strip would then be immersed in a solution 10 containing an antibody specific for the insect antigen (M) and conjugated to an enzymic (E) or other label 12. After washing 14 away unbound antibody-enzyme conjugate 12, the test strip 2 would be dipped in a solution 16 comprising a substrate(s) for the enzyme (E) which is converted by the enzyme into a colored product (or assayed for the other label). The test strip may then be removed from the solution and the production of a colored product 18 observed when the antibody-enzyme conjugate was bound to the test strip through an insect antigen. The extent of color development or other label would be proportional to the amount of insect antigen (such as myosin or a component thereof) present in the test solution.

Such test strip assays may utilize polyclonal, monoclonal or a mixture of monoclonal antibodies and a variety of enzyme labels and color-producing substrates to maximize the ease of use and sensitivity.

EXAMPLE 7

Detection of Insect Myosin in Grain Samples

The immunological procedures described above were used to detect insect myosin in samples of corn, soybean, rye, spring wheat, hard winter wheat, oats, hulled barley, whole barley, Wehani-rice and brown rice.

Ten grams of grain were ground in a small Waring blender. 20 ul of 0.5N NaCl was added and the mixture was stirred and mixed well. The mixture was then centrifuged for 10 min. at 15,000 g. The supernatants were used to prepare test samples by addition of purified cricket myosin in varying amounts, as indicated in FIGS. 17A-18B. The test samples were then assayed by the standard ELISA procedure. Antibody concentrations were as indicated on the FIGS. 17A-18B.

Figure 17A:
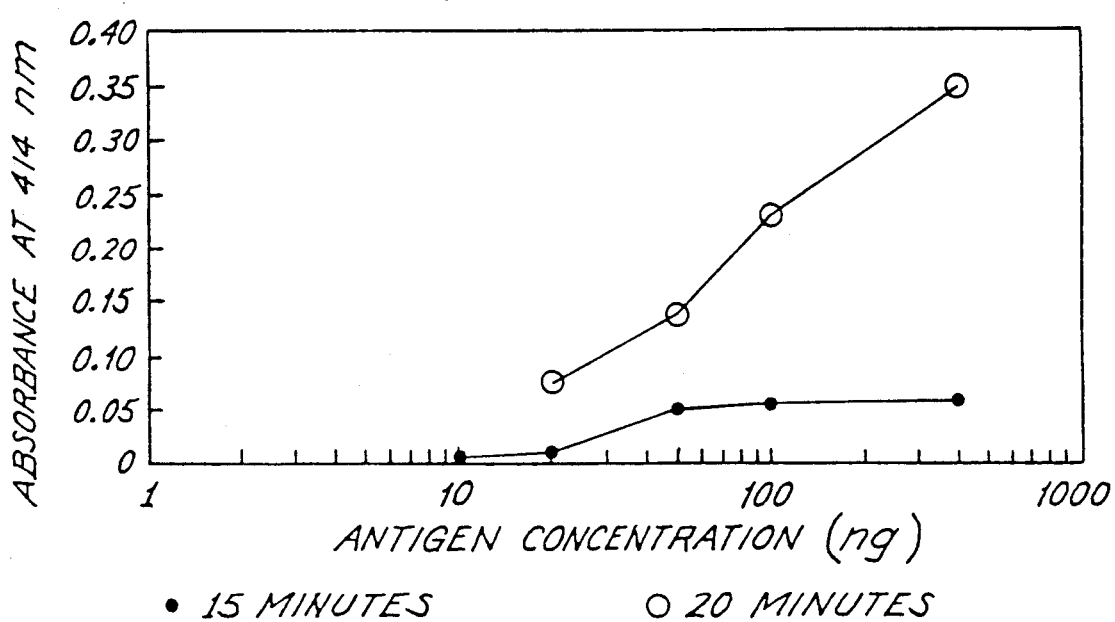
FIG. 17A shows, with an ELISA for grain insects using antibody to cricket myosin, the relationship of antigen concentration in soybean and ELISA response at 414 nm with a 1:1,000 antibody concentration for two reaction times.
Figure 17B:
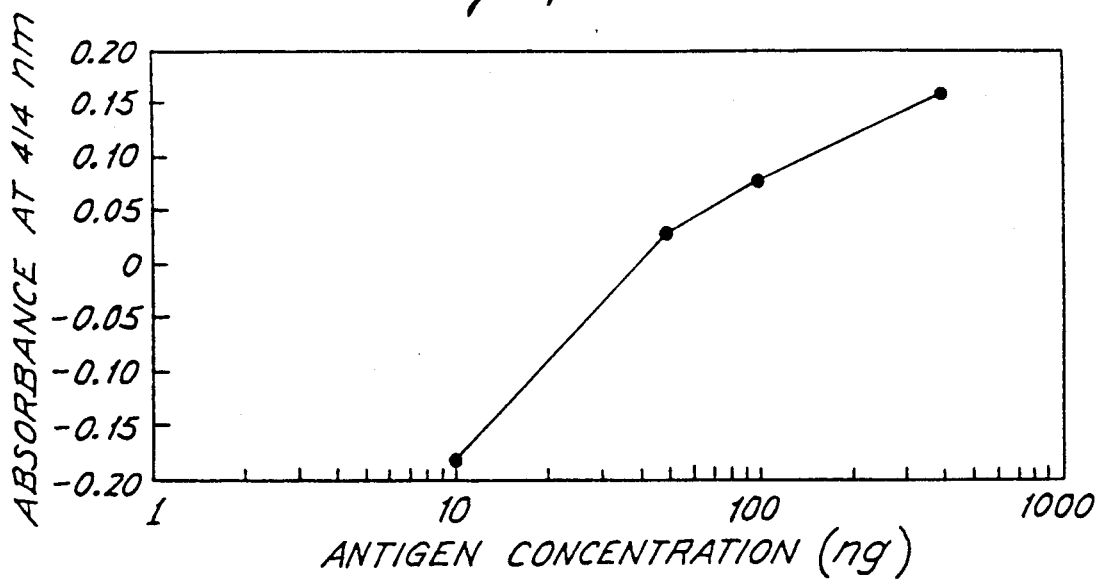
FIG. 17B shows, with an ELISA for grain insects using antibody to cricket myosin, the relationship of antigen concentration in soybean and ELISA response at 414 nm with a 1:10,000 antibody concentration.

FIG. 17A shows the relationship of antigen concentration in soybean and ELISA response at 414 nm with a 1:1000 serum antibody dilution. FIG. 17B shows the relationship of antigen concentration in soybean and ELISA response at 414 nm with a 1:10000 serum antibody dilution.

Figure 18A:
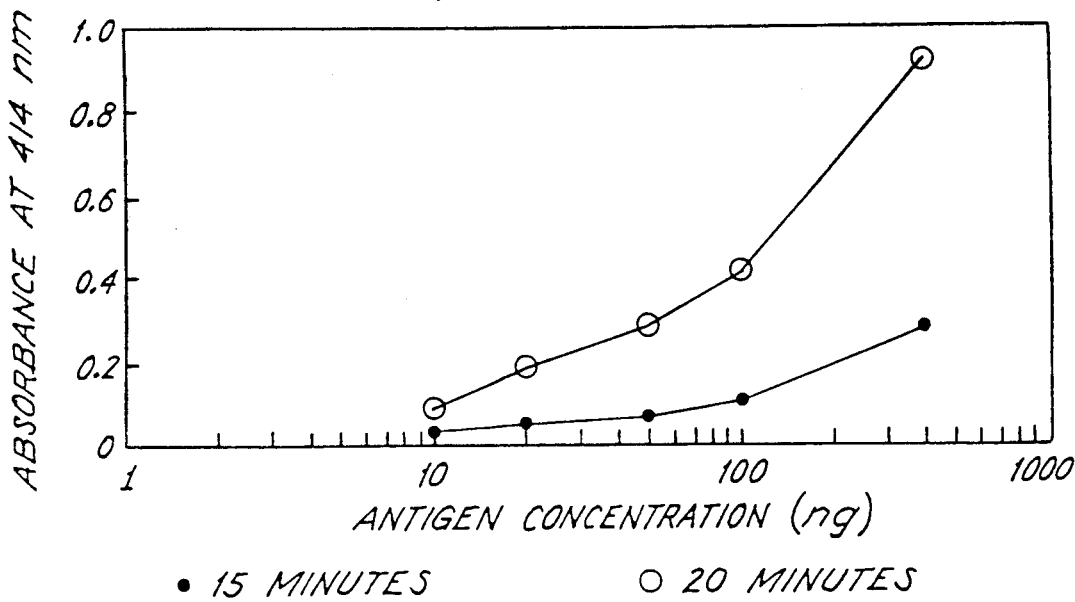
FIG. 18A shows the relationship of antigen concentration in wheat and ELISA response (anti-cricket myosin antibody) at 414 nm with a 1:1,000 antibody concentration.
Figure 18B:
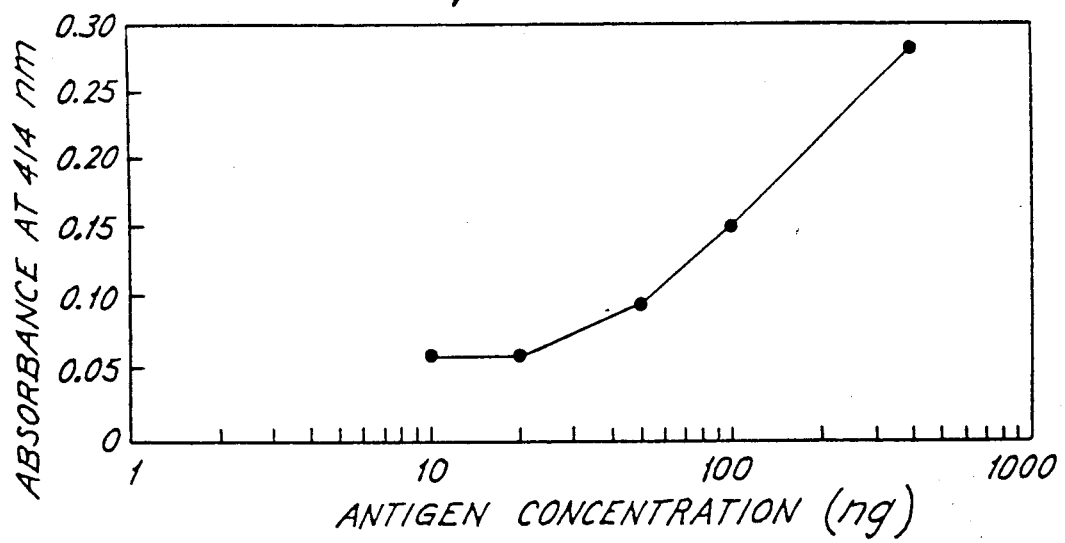
FIG. 18B shows the relationship of antigen concentration in wheat and ELISA response (anti-cricket myosin antibody) at 414 nm with a 1:10,000 antibody concentration.

FIG. 18A shows the relationship of antigen response concentration in wheat and ELISA at 414 nm with a 1:1000 serum antibody dilution. FIG. 18B shows the relationship of antigen concentration in wheat and ELISA response at 414 nm with a 1:10000 serum antibody dilution. Results analogous to those of 17A-18B were obtained from samples of the other grain, bean and corn foodstuffs listed above.

Figure 19:
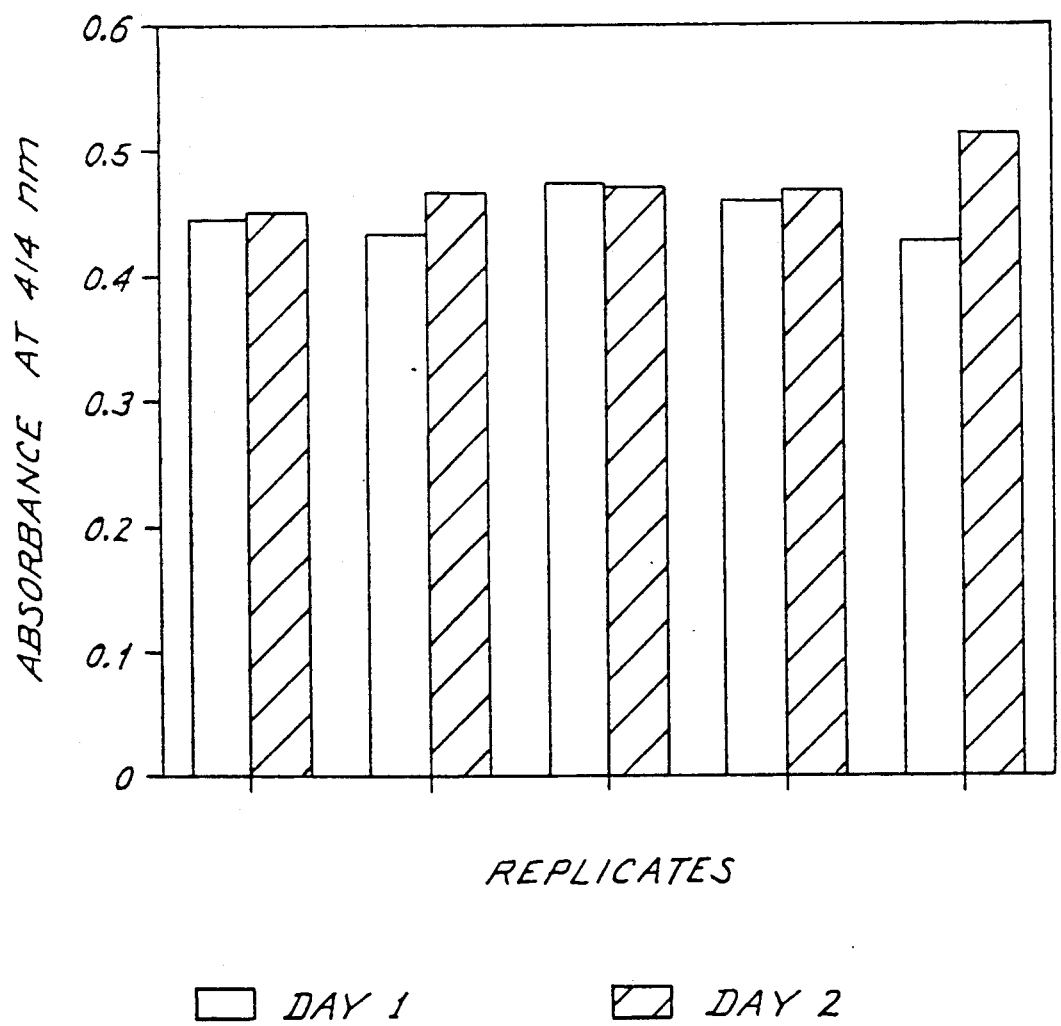
FIG. 19 illustrates the replicability detection of granary weevils (5 weevils/sample) in a grain mixture by immunoassay. The average was 0.45 and range 0.433 to 0.472.

Ten grams of grain were mixed with 5 granary weevils and ground in a small Waring blender. 20 ml of 0.5N NaCl was added and the mixture was stirred and mixed well. The mixture was then centrifuged for 10 min. at 15,000 g. The supernatant was used to prepare a test sample. Duplicate samples were assayed for ELISA response on five successive days (see FIG. 19).

EXAMPLE 8

Sandwich ELISA Procedure

Figure 20:
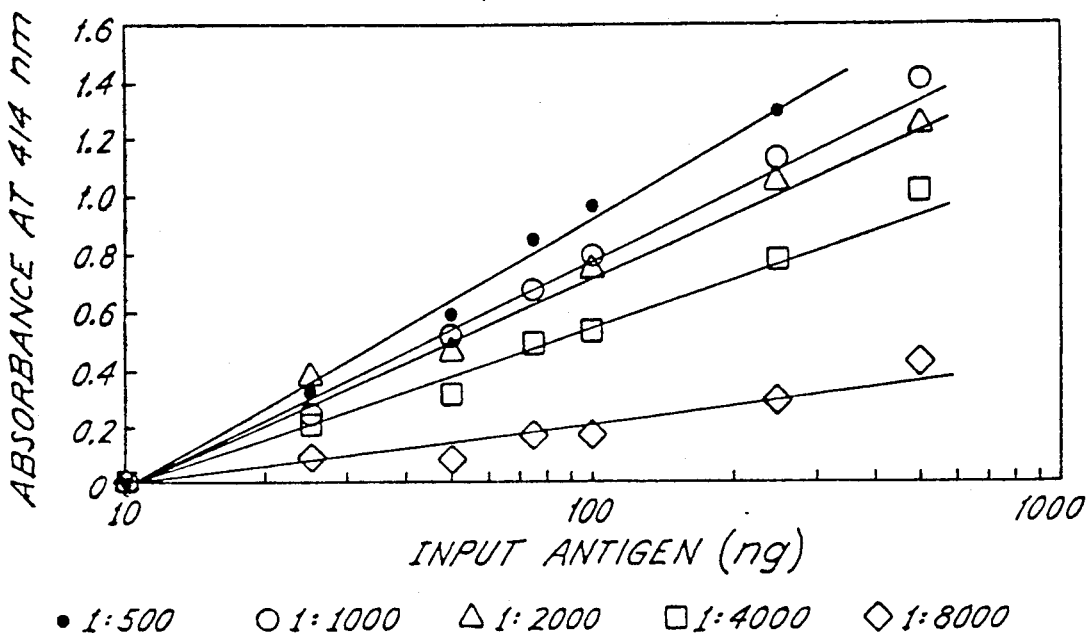
FIG. 20 shows the sandwich ELISA response over a series of insect antigen concentrations at various dilutions of capture antibody. The capture antibody (Ab) dilutions are shown for each symbol.
Figure 21:
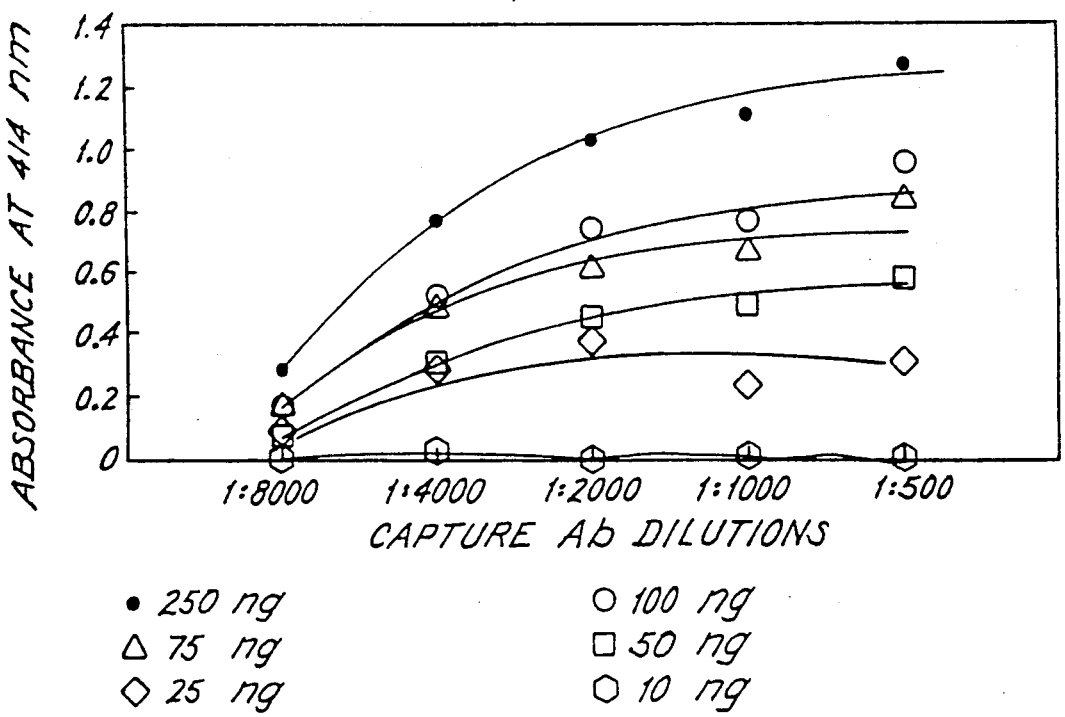
FIG. 21 illustrates the sandwich ELISA response at a series of capture antibody (capture Ab) dilutions and various antigen concentrations. The capture antibody dilutions are shown for each symbol.
Figure 22:
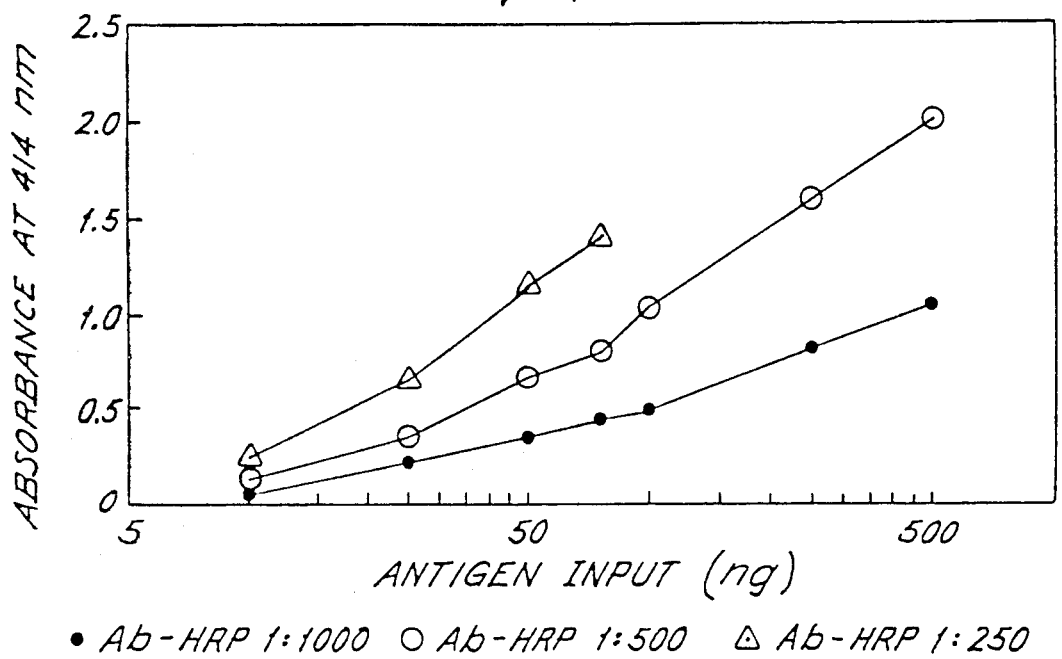
FIG. 22 schematically shows the sandwich ELISA response at a series of antigen concentrations and at various dilutions of antibody-horseradish peroxidase (Ab-HRP) conjugate. The Ab-HRP dilutions are shown for each symbol.
Figure 23:
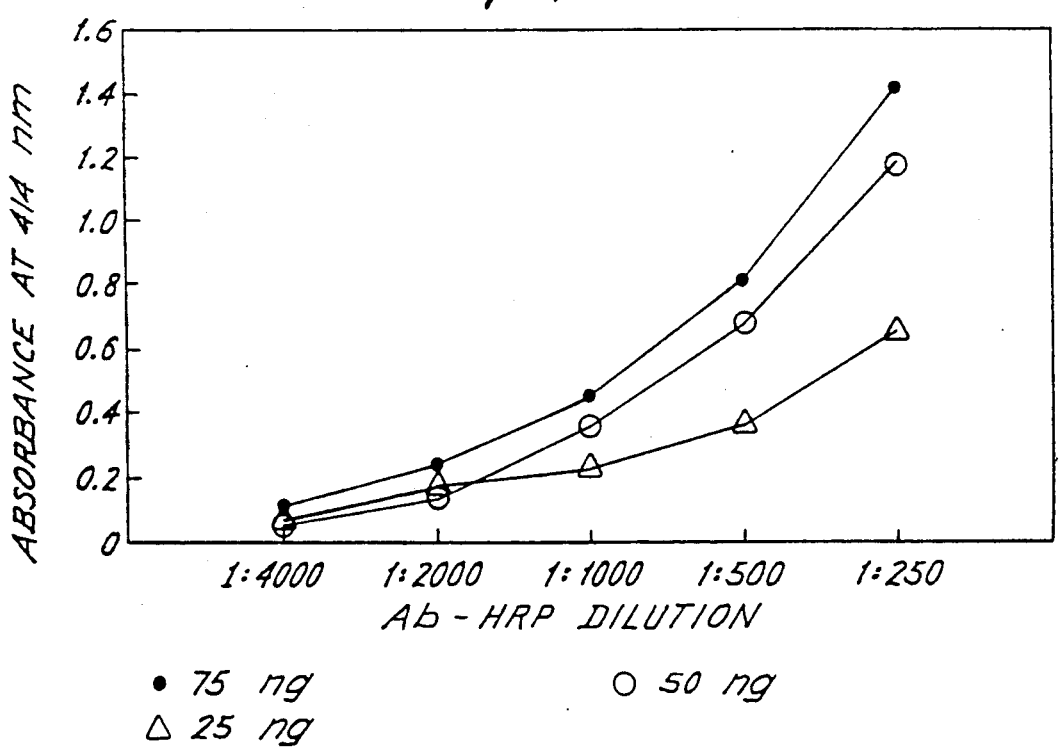
FIG. 23 illustrates the sandwich ELISA response at a series of Ab-HRP dilutions and at several antigen concentrations. The Ab-HRP dilutions are shown for each symbol.

Wells of a microtiter plate were coated with 50 ul of purified capture polyclonal antibody diluted (1:1000) in 0.15M sodium phosphate, pH 7.5. After a one hour incubation at room temperature, the wells were aspirated, and washed once with buffer HN. The wells were then incubated for one hour at room temperature with 100 ul buffer HNA. Afterwards, this solution was removed, and the wells washed twice with buffer HNAT. To each well was then added 50 ul of 0.15M sodium phosphate, pH 7.5/0.02% Tween-80, followed by 50 ul of the test solution, usually in 0.15M sodium phosphate, pH 7.5. After a 45 minute incubation at room temperature, the wells were emptied, and washed three times with buffer HNAT. Polyclonal antibody-horseradish peroxidase (HRP) conjugated by glutaraldehyde (1:500 dilution in HNAT) was then added to each well, followed by a thirty minute incubation at room temperature. The antibody conjugate was then removed, and the wells washed three times with buffer HNAT. To each well was then added 100 ul of the ABTS reaction mixture. After a reaction time of 15 minutes, the reaction was stopped by the addition of $NaN_3$, and the absorbance read at 414 nm. FIG. 20 shows the sandwich ELISA response over a series of insect antigen concentrations at various dilutions of capture antibody. FIG. 21 illustrates the sandwich ELISA response at a series of capture antibody dilutions and various antigen concentrations. FIG. 22 represents the sandwich ELISA response at a series of antigen concentrations with different dilutions of antibody-HRP conjugate. FIG. 23 shows the sandwich ELISA response at a series of Ab-HRP dilutions and at various antigen concentrations.

EXAMPLE 9

Sandwich ELISA in the Presence of Flour Spiked with Free Antigen

Five groups of five sample tubes were prepared containing 0, 50, 150, 300, and 600 mg of wheat flour. A sample of each group was then spiked with 2.5 ml of the following concentrations of antigen (crude cricket myosin) in 0.15M sodium phosphate, pH 7.5: 0 ng/ul, 0.5 ng/ul, 1 ng/ul, 1.5 ng./ul, 2 ng/ul. The sandwich ELISA was performed as above, and the data analyzed for the ability of the sandwich ELISA to perform in the presence of different amounts of flour.

Figure 24:
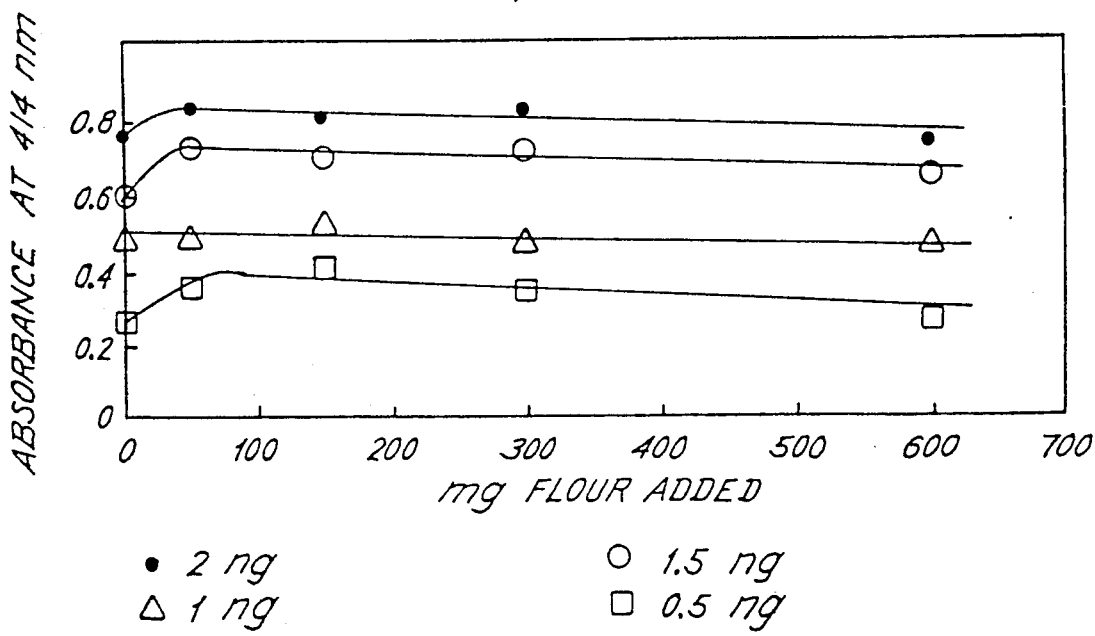
FIG. 24 shows the sandwich ELISA response at a series of flour levels with four different antigen concentrations. The antigen concentrations are shown for each symbol.
Figure 25:
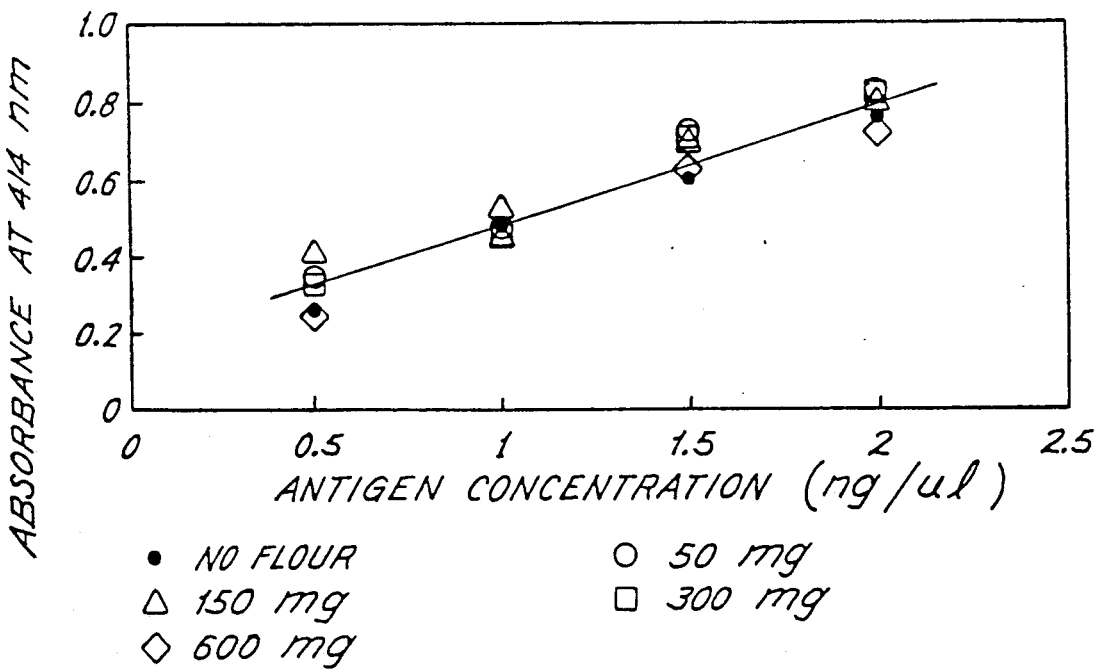
FIG. 25 illustrates sandwich ELISA response linearity at a series of antigen concentrations and at five flour levels. The amount of flour is shown for each symbol.

FIG. 24 shows the sandwich ELISA response at a series of flour concentrations with four different antigen concentrations. FIG. 25 illustrates sandwich ELISA response linearity at a series of antigen concentrations with five concentrations of flour.

EXAMPLE 10

Avidin/Streptavidin-Biotin ELISAs

Antibody Purification and Conjugation Procedure were conducted as follows: Antibodies were purified following an adaption of the method of Ey (35) on a three $cm^3$ column of immobilized (6% cross-linked beaded agarose) Protein A (Pierce). A 0.8 ml sample of serum (rabbit #780, Jun. 9, 1989) was combined with 2 ml column buffer (0.14M sodium phosphate, pH 8.0, 0.05% $NaN_3$), loaded on to the column, and incubated for 10 minutes. Column buffer was then passed through the column at a flow rate of 0.4 ml/min., and 1.0 ml fractions were collected until the absorbance at 280 nm of the fractions returned to about zero (23 fractions). Elution buffer (0.1M sodium citrate/citric acid, pH 4.0, 0.05% NaN ) was then passed through the column, and fractions collected until their absorbances at 280 nm returned to 0. Peak fractions corresponding to purified IgG from three runs were pooled to yield 17.6 ml of a solution with an absorbance at 280 nm of 1.189, and a calculated protein concentration of 0.87 mg/ml. This solution was then brought to 50% $(NH_4)_2SO_4$ saturation at 0° C. by the addition of 5.18 g of powdered $(NH_4)_2SO_4$ with stirring over a 25 minute period, followed by an additional 25 minutes of stirring on ice. After centrifugation at 20,000 xg for 20 minutes, the resulting pellet was resuspended in 0.75 ml of 0.15M sodium phosphate, pH 7.5 to give a solution approximately 20 mg/ml IgG.

The conjugation procedure used is a modification of the procedure of Engvall (36), which is based upon the original procedure of Avrameas and Ternynck (37). Horseradish peroxidase (HRP, EC 1.11.1.7, Sigma lot 66F-9700-1) was dissolved in 0.2 ml 1.25% technical grade glutaraldehyde (Sigma, 25% glutaraldehyde diluted in 0.15M sodium phosphate, pH 7.2, 0.15M NaCl) in a glass test tube, and left at room temperature, in the dark, for 17 hours. The next day, the reaction mixture was diluted to 1.0 ml with 0.1M sodium carbonate buffer, pH 9.2, and dialyzed at 4° C. against two 1.0 L changes of this buffer. The purified IgG was also dialyzed at this time. After the dialysis, 0.25 ml of the IgG solution was added to the HRP solution (in a glass test tube), and allowed to incubate at room temperature for 15 hours. The next day, 0.2 ml of 0.2M lysine was added to the reaction mixture, shaken, and allowed to sit at 4° C. for 4 hours. The reaction mixture was then made 50% in glycerol, and stored as aliquots at −80° C.

Although avidin-biotin linked ELISAs have not yet been applied to insect contamination studies, the technology is widely used and the materials are readily available. Adaptation of the present ELISA to this format should prove fairly routine.

Avidin is a homotetrameric, 66,000 molecular weight glycoprotein which has a very strong, selective, and stable affinity for the small molecule biotin (38). Avidin is capable of binding four biotin molecules, and the dissociation constant ($K_d$) for the avidin-biotin complex is $10^{-15}$M (39); this is several orders of magnitude higher than the range of typical $K_d$s for antigen-antibody complexes ($10^{-6}$ to $10^{-11}$M. Both biotin and avidin can be covalently linked to proteins, while maintaining the avidin-biotin interaction, as well as protein function. Not surprisingly, a large number of immunoassays have been developed which take advantage of these unique properties. Most of these immunoassays use a form of avidin known as streptavidin, isolated from *Streptomyces avidinii*. Streptavidin is a 60,000 molecular weight protein that lacks the glycoprotein moiety of avidin, this leads to a much reduced background (when compared to avidin) in several types of assays (40, 41).

There are two basic types of biotin-streptavidin immunoassays. In the first type of assay, a biotinylated antibody is used to detect the antigen of interest. The antigen may be either immobilized on some solid support (indirect ELISA) or bound to a capture antibody (sandwich ELISA). The biotinylated antibody bound to the antigen is then detected using an enzyme labeled streptavidin. Addition of substrate for the enzyme produces a detectable color proportional to the amount of antigen initially present. In the second type of assay, a "bridge" is formed between biotinylated antibody and biotinylated label by streptavidin. The initial procedure is as above, however, in place of labeled streptavidin, unconjugated streptavidin is added, followed by the addition of labeled biotin. Although this assay has an extra step, this extra step can lead to increased sensitivity in the detection of antigen.

The following literature citations are incorporated by reference in pertinent part herein for the reasons cited in the above text.

REFERENCES

1. Trauba (1981), Determination of Internal Insect Infestation in Wheat: Collaborative Study, J. Assoc. Off. Anal. Chem., 64(6):1408-1410
2. Parker et al (1982), Sampling, Inspection, and Grading of Grain, in *Storage of Cereal Grains and Their Products*, Chapter 1, pp. 1-35, American Association of Cereal Chemists.
3. Milner et al. (1950), Application of X-Ray Technique to the Detection of Internal Insect Infestation of Grain. J. Econ. Entomol., 43:933-935.
4. Street (1971), Nuclear Magnetic Resonance for Detecting Hidden Infestation in Stored Grains, J. Georgia Entomolog. Soc., 6(4):249:254.
5. Chambers et al. (1984), Nuclear Magnetic Resonance for Studying the Development and Detection of the Grain Weevil Sitophilus granarious (L.) (Coleoptera: Curculionidae) Within Wheat Kernels. Bull. Ent. Res., 74:707-724.
6. Chambers (1987), Recent Developments in Techniques for the Detection of Insect Pests of Stored Products. BCPC Mono. No. 37 Stored Products Pest Control. 151-166.
7. Adams et al. (1953), Aural Detection of Grain Infested Internally With Insects. Science, 118:163-164.
8. Street et al. (1976), $CO_2$ Analyzer Detects Insects Hidden in Foods. Fd. Engng., 48:94-95.
9. Ashman et al. (1969), An Instrument for detecting Insects Within Food Grains. Milling, 151:32-36.
10. Webb et al. (1988), A Computerized Acoustical Larval Detection System. Applied Engineering in Agriculture, 4:268-274.
11. Webb et al. (1988), Acoustical System to Detect Larvae in Infested Commodities. The Florida Entomologist, 71:492-504.
12. Vick et al. (1988), Sound Detection of Stored-Produce Insects That Feed Inside Kernels of Grain. J. Econ. Entomol., 81(5):1489-1493.
13. Monroe (1984), Enzyme Immunoassay, anal. Chem., 56(8):920A-931A.
14. Shoham et al. (1987), New Immunochemical Method for Rapid Detection of Human Chriogonadotropin in Urine, Clinical Chemistry, 33(6):800-802.
15. Klausner (1987), Immunoassays Flourish in New Markets, Bio/technology, 5(6):551-556.
16. Emerson et al. (1987) Molecular Genetics of Myosin. Ann. Rev. Biochem., 56:695-726.
17. Richards et al. (1946), Correlation Between the Possession of Chitinous Cuticle and Sensitivity to DDT. Biol. Bull. 90-107.
18. Prakasam et al. (1975), An Optimum pH for the Demonstration of Chitin in *Periplaneta Americana* Using Lugol's Iodine. Acta Histochem., 53:238-240.
19. Reissig et al. (1955), A Modified Colorimetric Method for the Estimation of N-Acetyl-Amino Sugars. J. Biol. Chem., 217:959-966.
20. Ride et al. (1971), A Chemical Method for Estimating *Fusarium oxysporum f. lycopersici* in infected tomato plants. Physiol Plant Pathol., 1:409-420.
21. Tsuji et al. (1969), Analytical Chemical Studies of Amino Sugars. Determination of Hexosamines Using 3-Methyl-2-Benzothiazolone Hydrazone Hydrochloride. Chem. Pharm. Bull., 17:1505-1510.
22. Wadsworth et al. (1984), Chitinolytic Activity of Commercially Available Beta-Glycosidase in "Chitin, Chitosan and Related Enzymes", J. P. Zikakis ed., Academic Press, 181-190.
23. Chaplain et al. (1966), The Mass of Myosin per Cross-bridge in Insect Fibrillar Flight Muscle, J. Mol. Biol., 21:275-280.

24. Woods et al. (1963). Studies on the Structure of Myosin in Solution. J. Biol. Chem., 238 (3):2374-2385.
25. Wang et al. (1984). Titin is an Extraordinarily Long, Flexible, and Slender Myofibrillar Protein. Proc. Natl. Acad. Sci. USA. 81:3685-3689.
26. Webber et al. (1969). The Reliability of Molecular Weight Determinations by Dodecyl Sulfate Polyacrylamide Gel Electrophoresis. J. Biol. Chem., 244(16):4406-4412.
27. Bradford (1976). A Rapid and Sensitive Method for the Quantitation of Microgram Quantities of Protein Using the Principle of Protein-Dye Binding. Anal. Biochem., 72:248-254.
28. Hunter et al. (1986). Immunological and Biosynthetic Studies on the Mammalian 2-oxoglutarate Dehydrogenase Multienzyme Complex. Europ. J. Biochem., 155:103-109.
29. Hurn et al. (198). Production of Reagent Antibodies. Methods in Enzymology, 70:104-102.
30. Browning et al. (1987). Identification of Two Messenger RNA Cap Binding Proteins in Wheat Germ. J. Biol. Chem., 262(23):1128-11232.
31. Levine et al. (1982). Preparation and Assay of Paramyosin. Methods in Enzymology, 85(16):149-164.
32. Wang et al. (1984). Titin is an Extraordinarily Long, Flexible, and Slender Myofibrillar Protein. Proc. Natl. Acad. Sci. USA. 81:3685-3689.
33. Monroe et al. (1985). The Solid Phase Enzyme Linked Immunospot Assay: Current and Potential Applications. BioTechniques May/Jun. 222-229.
34. Bahr et al. (1980). Immunology. 41:865-873.
35. Ey (1978). Isolation of Pure $IgG_1$, $IgG_{2a}$, and $IgG_{2b}$ Immunoglobulins from Mouse Serum Using Protein-A Sepharose. Immunochem., 15:429-436.
36. Engvall (1980). Enzyme Immunoassay ELISA and EMIT. Methods in Enzymology, 70:418-439.
37. Avrameas et al. (1971). Peroxidase labeled antibody and Fab conjugates with enhanced intracellular penetration. Immunochem., 8:1175-1179.
38. Green et al. (1975). In: Advances in Protein Chemistry. C. B. Anfinsen, ed., 29:85.
39. Green (1963). Avidin. Biochem. J., 89:593-620.
40. Gardner (1983). Biotechniques, 1:39.
41. Haeuptle et al., (1983). Binding Sites for Lactogenic and Somatogenic Hormones from Rabbit Mammary Gland and Liver. J. Biol. Chem., 258:305.

What is claimed is:

1. A method for determining a degree of insect contamination in a foodstuff, the method comprising:
obtaining an antibody specifically binding insect myosin or an insect myosin component antigen;
incubating a sample of said foodstuff with the antibody;
determining an extent of antibody-antigen interaction by an ELISA; and
correlating the extent of interaction with a degree of insect contamination in said foodstuff.

2. The method of claim 1 wherein the component is a myosin heavy chain.

3. A method for determining the degree of insect contamination in a foodstuff, the method comprising:
subjecting a sample of foodstuff to conditions sufficient to at least partially solubilize insect myosin or components thereof contained therein;
measuring by an ELISA insect myosin or myosin comopnent content of said sample; and
correlating the insect myosin or insect myosin component content with a degree of insect contamination in said foodstuff.

4. The method of claim 1 or 3 wherein the foodstuff is a whole grain, a milled grain, a spice, coffee or a prepared food.

5. A method for determining a degree of insect contamination in a whole or milled grain, the method comprising:
obtaining an antibody specifically binding an insect myosin or a component thereof;
incubating a sample or extract of said whole or milled grain with the antibody;
determining an extent of antibody interaction with said sample or extract by an ELISA; and
correlating said extent of interaction with a degree of insect contamination in the whole or milled grain.

6. The method of claim 1, or 3 wherein the antibody is a monoclonal antibody or mixture of monoclonal antibodies.

7. The method of claim 1, or 5, wherein the antibody is a polyclonal antibody or mixture of polyclonal antibodies.

8. A method for determining a degree of insect contamination in a whole or milled grain, the method comprising:
measuring by an ELISA a content of insect myosin or component thereof in a sample of said whole or milled grain; and
calculating from said content of insect myosin or component thereof a degree of insect contamination in said whole or milled grain.

9. A method for determining the degree of insect contamination in a whole or milled grain, the method comprising:
subjecting a sample of said whole or milled grain to conditions sufficient to at least partially solubilize insect myosin or comopnent thereof contained therein;
measuring by ELISA an insect myosin content or insect myosin component content of said sample; and
correlating the myosin content or myosin component content with an estimated degree of insect contamination in said whole or milled grain.

10. The method of claim 1, 3, 5, 8, or 9 wherein the insect contamination comprises at least one of:
Sitophilus zeamais;
Sitophilus granarius;
Sitophilus oryzae;
Trogoderma variabile;
Trogoderma glabrum;
Tribolium castaneum;
Tribolium confusem;
Oryzaephilus mercaptor;
Oryzaephilus surinamensis;
Rhyzopertha dominica;
Prostephanus truncatus;
Lasioderma serricorne;
Stegobium paniceum;

11. A kit useful for the detection of insect contamination in a foodstuff which comprises:
a carrier being compartmentalized to receive one or more container means in close confinement therein;
a first container means comprising an antibody specifically binding insect myosin or component thereof, said antibody being affixed to a solid matrix; and a second container means comprising detectably labeled antibody specifically binding insect myosin or component thereof.

12. A kit useful for the detection of insect contamination in a foodstuff which comprises:
a carrier being compartmentalized to receive one or more container means in close confinement therein:
a first container means comprising an antibody from a first antibody-producing species, said antibody specifically binding insect myosin or component thereof; and
a second container means comprising a detectably labeled antibody from a second antibody-producing species, said detectably labeled antibody specifically binding antibody from the first antibody-producing species.

13. The kit of claims 11 or 12 wherein said component is an insect myosin heavy chain.

14. The kit of claim 11 or 12 wherein said detectably labeled antibody is labeled with a radiolabel, an enzyme label, a fluorescent label or a chromophore.

15. A method of determining the amount of insect contamination in grain, the method comprising the steps of:
preparing a solution or suspension from a homogenized grain sample;
substantially affixing at least a portion of said solution or suspension to a solid surface;
applying to said solid surface an antibody conjugated with a label, said antibody specifically binding insect myosin or components thereof and said enzyme catalyzing formation of a colored product from a substrate;
washing unbound conjugate from the solid surface;
measuring label bound to the surface; and
correlating amounts of bound label with an amount of insect contamination.

16. The method of claim 15 wherein the antibody is conjugated with an enzyme label and the bound antibody-enzyme conjugate is measured by incubating the solid surface with an enzyme substrate under conditions allowing colored product to be formed when enzyme is present.

17. A method of determining the amount of insect contamination in grain, the method comprising the steps of:
affixing to a solid surface a capture antibody having specific binding affinity for insect myosin or component thereof;
blocking nonspecific absorption sites on the surface by incubation with protein not specifically binding insect myosin, insect myosin component or the antibody;
preparing an aqueous solution or suspension of a homogenized grain sample;
applying at least a portion of said solution or suspension to the solid surface to facilitate binding of insect myosin or comopnent thereof to the affixed antibody;
washing the solid surface;
applying to said solid surface an antibody conjugated with a label, said conjugate antibody specifically binding the insect myosin or component thereof;
washing unbound conjugate from the solid surface;
measuring label bound to said surface; and
correlating amounts of bound label with an amount of insect contamination.

18. The method of claim 15 or 17 wherein said component is an insect myosin heavy chain.

19. The method of claim 17 wherein at least one of the capture antibody and conjugate antibody is polyclonal.

20. The method of claim 17 wherein at least one of the capture antibody and conjugate antibody is monoclonal or a mixture of monoclonals.

21. The method of claim 17 wherein the antibody is conjugated to an enzyme label and the label is measured by incubating the solid surface with an enzyme substrate under conditions allowing colored product to be formed when enzyme is present.

22. The method of claim 21 wherein the enzyme is a peroxidase.

23. The method of claim 17 wherein the capture antibody and antibody conjugate bind to different insect myosin epitopes.

24. The method of claim 17 wherein the label is an enzyme catalyzing formation of a colored product from a substrate.

25. A method of determining the amount of insect contamination in a sample of grain, the method comprising the steps of:
preparing an aqueous solution or suspension from a homogenized grain sample;
contacting a solid surface with said solution or suspension to substantially affix at least a portion of insect myosin or comopnent thereof in said solution or suspension to the solid surface;
incubating said solid surface with a first antibody from a first animal species, said first antibody specifically binding insect myosin or component thereof;
washing unbound first antibody from the solid surface;
blocking nonspecific absorption sites on the solid surface by chemical reaction or with protein not specifically binding insect myosin, insect myosin component or the first antibody;
applying to said solid surface a labeled second antibody, said second antibody being from a second animal species, specifically binding the first antibody from the first animal species and said label being a fluorescent compound, radioisotope, or chromophoric compound or an enzyme catalyzing formation of a colored product from a substrate;
washing unbound labeled second antibody from the solid surface;
determining an amount of labeled second antibody bond to said washed solid surface; and p1 correlating the amount of bound labeled second antibody with an amount of insect contamination in said grain, said amount of bound labeled second antibody being proportional to insect myosin or component thereof in the grain sample.

26. A method of determining the amount of insect contamination in a sample of grain, the method of comprising the steps of:
preparing an aqueous solution or suspension from a homogenized grain sample;
contacting a solid surface with said solution or suspension to substantially affix at least a portion of insect myosin or component thereof in said solution or suspension to the solid surface;
incubating said solid surface with a first antibody from a first animal species, said first antibody specifically binding insect myosin or component thereof;

washing unbound first antibody from the solid surface;

blocking nonspecific binding sites on the solid surface by chemical reaction or incubation with protein not specifically binding insect myosin, myosin component or first antibody;

applying to said solid surface a labeled second antibody, said second antibody being from a second animal species, specifically binding the first antibody from the first animal species and said label being an enzyme catalyzing formation of a colored product from a substrate;

washing unbound labeled second antibody from the solid surface;

incubating the solid surface with an enzyme substrate so that colored product is formed proportional to when enzyme label present; and correlating amounts of color formed with an amount of insect contamination, said color formation being indicative of an amount of insect contamination in the grain sample.

27. A method of determining the amount of insect contamination in grain, the method comprising the steps of:

affixing to a solid surface a capture antibody having specific binding affinity for insect myosin or component thereof;

blocking nonspecific binding sites on said surface by chemical reaction or incubation with protein not specifically binding capture antibody, insect myosin or insect myosin component;

preparing an aqueous solution or suspension of a homogenized grain sample;

applying at least a portion of said solution or suspension to the solid surface to facilitate binding of insect myosin or insect myosin component contained therein to the affixed capture antibody;

washing the solid surface to remove unbound components of the solution or suspension;

applying to said solid surface an antibody-enzyme conjugate, said conjugate antibody specifically binding the insect myosin or insect myosin component and said enzyme catalyzing formation of a colored product from a substrate;

washing unbound conjugate from the solid surface;

incubating the solid surface with an enzyme substrate, allowing colored product to be formed when enzyme of the conjugate is present; and correlating colored product formed with an amount of insect contamination, color formation being proportional to an amount of insect myosin or insect myosin component in the grain sample.

28. A method of determining the amount of insect contamination in a grain sample, the method comprising the steps of:

preparing an aqueous solution or suspension from a homogenized grain sample;

contacting a solid surface with said solution or suspension to substantially affix at least a portion of insect myosin or insect myosin component in said solution or suspension to the solid surface;

incubating said solid surface with biotinylated antibody, said biotinylated antibody specifically binding insect myosin or insect myosin component;

washing unbound biotinylated antibody from the solid surface;

applying labeled avidin to said washed solid surface, said avidin specifically binding the biotinylated antibody and said label being a detectable substance which is a fluorescent compound, radioisotope, chromophoric compound or an enzyme catalyzing formation of a colored product from a substrate;

washing unbound labeled avidin from the solid surface;

determining an amount of labeled avidin bound to said washed solid surface; and correlating the amount of bound labeled avidin with an amount of insect contamination in said grain, said amount of bound labeled avidin being proportional to insect myosin or insect myosin component in the grain sample.

29. The method of claim 25, 26, 27, or 28 wherein the enzyme is a peroxidase.

30. The method of claim 25, 26, 27, or 28 wherein at least one antibody is polyclonal.

31. The method of claim 25, 26, 27, or 28 wherein at least one antibody is monoclonal or a monoclonal mixture.

32. A method for integrated pest management comprising identifying an amount or type of insect pest present in a growing crop by assaying a sample of said crop by an immunospecific assay for insect myosin or an insect myosin component and relating the result of said assay to the amount or type of insect pest present in said sample.

* * * * *

UNITED STATES PATENT AND TRADEMARK OFFICE
CERTIFICATE OF CORRECTION

Page 1 of 2

PATENT NO. : 5,118,610
DATED : June 2, 1992
INVENTOR(S) : G. Barrie Kitto, Frank A. Quinn, Wendell Burkholder It is certified that error appears in the above-indentified patent and that said Letters Patent is hereby corrected as shown below:

In claim 3, column 23, line 68, delete the term "comopnent" and insert the term --component-- therefor.

In claim 6, column 24, line 18, delete the numeral "3" and insert the numeral --5-- therefor.

In claim 9, column 24, line 39, delete the term "comopnent" and insert the term --component-- therefor.

In claim 10, column 24, line 56, delete the term "mercaptor" and insert the term --mercator-- therefor.

In claim 10, column 24, line 62, append the following description --callosobruchus maculatus;
   attagenus megatoma;
   Alphitobius diaperinus; or
   Plodia interpunctella.--.

In claim 17, column 25, line 59, delete the term "component" and insert the term --component-- therefor.

In claim 25, column 26, line 29, delete the term "comopnent" and insert the term --component-- therefor.

In claim 25, column 26, line 52, delete the term "bond" and insert the term --bound-- therefor.

In claim 25, column 26, line 52, delete the term "p1" and begin new paragraph.

In claim 26, column 26, line 59, immediately following the term 'method' delete the term "of".

UNITED STATES PATENT AND TRADEMARK OFFICE
CERTIFICATE OF CORRECTION

PATENT NO. : 5,118,610

DATED : June 2, 1992

INVENTOR(S) : G. Barrie Kitto, Frank A. Quinn, Wendell Burkholder

It is certified that error appears in the above-indentified patent and that said Letters Patent is hereby corrected as shown below:

In claim 26, column 27, line 21, immediately before the term 'enzyme', delete the term "when".

Signed and Sealed this

Thirty-first Day of August, 1993

Attest:

BRUCE LEHMAN

*Attesting Officer*   *Commissioner of Patents and Trademarks*